US012139766B2

(12) United States Patent
Di Fiore et al.

(10) Patent No.: US 12,139,766 B2
(45) Date of Patent: *Nov. 12, 2024

(54) METHODS AND KITS COMPRISING GENE SIGNATURES FOR STRATIFYING BREAST CANCER PATIENTS

(71) Applicants: Istituto Europeo di Oncologia S.r.l., Milan (IT); Fondazione Istituto Firc di Oncologia Molecolare (IFOM), Milan (IT); Universita degli Studi di Milano (University of Milan), Milan (IT)

(72) Inventors: Pier Paolo Di Fiore, Milan (IT); Salvatore Pece, Milan (IT); Manuela Vecchi, Milan (IT); Stefano Confalonieri, Milan (IT)

(73) Assignees: Istituto Europeo di Oncologia S.r.l., Milan (IT); Fondazione Istituto Firc di Oncologia Molecolare (IFOM), Milan (IT); Universita degli Studi di Milano (University of Milan), Milan (IT)

( * ) Notice: Subject to any disclaimer, the term of this patent is extended or adjusted under 35 U.S.C. 154(b) by 0 days.

This patent is subject to a terminal disclaimer.

(21) Appl. No.: 17/816,210

(22) Filed: Jul. 29, 2022

(65) Prior Publication Data
US 2023/0151428 A1    May 18, 2023

Related U.S. Application Data

(63) Continuation of application No. 16/308,564, filed as application No. PCT/EP2017/064937 on Jun. 19, 2017, now Pat. No. 11,441,191.

(30) Foreign Application Priority Data

Jun. 20, 2016  (EP) ..................... 16175354
Sep. 14, 2016  (EP) ..................... 16188855

(51) Int. Cl.
C12Q 1/68     (2018.01)
C12P 19/34    (2006.01)
C12Q 1/6886   (2018.01)
G16B 5/00     (2019.01)
G16B 40/00    (2019.01)

(52) U.S. Cl.
CPC ..... *C12Q 1/6886* (2013.01); *C12Q 2600/106* (2013.01); *C12Q 2600/112* (2013.01); *C12Q 2600/118* (2013.01); *C12Q 2600/158* (2013.01); *C12Q 2600/16* (2013.01); *C12Q 2600/166* (2013.01); *G16B 5/00* (2019.02); *G16B 40/00* (2019.02)

(58) Field of Classification Search
CPC ............ C12Q 1/6886; C12Q 2600/118; C12Q 2600/16; C12Q 2600/158; C12Q 2600/106; C12Q 2600/166; C12Q 2600/112
See application file for complete search history.

(56) References Cited

U.S. PATENT DOCUMENTS 11,441,191  B2   9/2022  Di Fiore et al.
2011/0172928 A1  7/2011  Gehrmann et al.
2019/0161809 A1  5/2019  Di Fiore et al.

FOREIGN PATENT DOCUMENTS

WO  WO-2008037700 A2  4/2008
WO  WO-2010003771 A1  1/2010
WO  WO-2017220492 A1  12/2017

OTHER PUBLICATIONS

Ozlem Yersal and Sabri Barutca, "Biological subtypes of breast cancer: Prognostic and therapeutic implications" World J Clin Oncol. Aug. 10, 2014; 5(3): 412-424. (Year: 2014).*
Barczak A. et al. "UCSF 4Hs version 2 human long oligo array", Gene Expression, 2003, 397 pages. probes ID: HD200001112, H200005758, HD200007211.
Chen, G. et al. "Discordant Protein and mRNA Expression in Lung Adenocarcinomas" Molecular & Cellular Proteomics 1.4, p. 304-313. (Year: 2002).
Cheung et al., "Natural variation in human gene expression assessed in lymphoblastoid cells." Nature Genetics, 33:422-425 (2003).
Cobb, J.P. et al. "Sepsis gene expression profiling: Murine splenic compared with hepatic responses determined by using complementary DNA microarrays" Crit Care Med 2002 vol. 30, No. 12, p. 2711-2721.
Desmedt, C. et al. "Strong time dependence of the 76-gene prognostic signature for node-negative breast cancer patients in the TRANSBIG multicenter independent validation series", Clinical Cancer Research, 2007, vol. 13, p. 3207-3214.
Geffen, D. B. et al. "The impact of the 21-gene recurrence score assay on decision making about adjuvant chemotherapy in early-stage estrogen-receptor-positive breast cancer in an oncology practice with a unified treatment policy", Annals of Oncology, 2011, vol. 22, p. 2381-2386.
Goldhirsch, A. et al. "Personalizing the treatment of women with early breast cancer: highlights of the St Gallen International Expert Consensus on the Primary Therapy of Early Breast Cancer", Annals of Oncology, 2013, vol. 24, p. 2206-2223.
Haibe-Kains, B. et al. "Comparison of prognostic gene expression signatures for breast cancer", BMC Genomics, 2008, vol. 9, p. 394.
Harrell, F. E., Jr., et al. "Multivariable prognostic models: issues in developing models, evaluating assumptions and adequacy, and measuring and reducing errors", Statistics in Medicine, 1996, vol. 15, p. 361-387.
Hoshikawa et al. "Hypoxia induces different genes in the lungs of rat compared with mice" Physical Genomics 2003; 12:209-219.
Huang, Z. et al. "Identification of Gene Expression Pattern Related to Breast Cancer Survival Using Integrated TCGA Datasets and Genomic Tools", Biomed Research International, vol. 34, No. 6, 2015, pp. 2833-2910.
International Preliminary Report on Patentability issued in PCT/EP2017/064937 dated Dec. 25, 2018, 8 pages.

(Continued)

*Primary Examiner* — Stephen T Kapushoc
(74) *Attorney, Agent, or Firm* — COOLEY LLP

(57) ABSTRACT

The present invention relates to refined prognostic clinical tools, methods, and kits for the evaluation of risk and treatment of distant recurrence in ER+/HER2− breast cancer patients.

6 Claims, 9 Drawing Sheets

Specification includes a Sequence Listing.

(56) References Cited

OTHER PUBLICATIONS

International Search Report and Written Opinion issued in PCT/EP2017/064937 dated Sep. 15, 2017, 12 pages.
Ivshina, A. V. et al. "Genetic reclassification of histologic grade delineates new clinical subtypes of breast cancer", Cancer Research, 2006, vol. 66, p. 10292-10301.
Karlsson E. et al. "The mTOR effectors 4EBP1 and S6K2 are frequently coexpressed, and associated with a poor prognosis and endocrine resistance in breast cancer: a retrospective study including patients from the randomised Stockholm tamoxifen trials", Breast Cancer Research, vol. 15, No. 5, 2013, p. R96.
Loi, S. et al. "Predicting prognosis using molecular profiling in estrogen receptor-positive breast cancer treated with tamoxifen", BMC Genomics, 2008, vol. 9, p. 239.
Paik S et al. "A multigene assay to predict recurrence of tamoxifen-treated, node-negative breast cancer", N Engl J Med. 2004, vol. 351, No. 27, p. 2817-2826.
Pawitan, Y. et al. "Gene expression profiling spares early breast cancer patients from adjuvant therapy: derived and validated in two population-based cohorts", Breast Cancer Research, 2005, vol. 7, p. R953-964.
Pece, S. et al. "Biological and molecular heterogeneity of breast cancers correlates with their cancer stem cell content", Cell, 2010, vol. 140, p. 62-73.
Sorlie, T. et al. Gene expression patterns of breast carcinomas distinguish tumor subclasses with clinical implications Proc Natl Acad Sci USA, 2001, vol. 98, p. 10869-10874.
Sotiriou C. et al. "Gene Expression Profiling in Breast Cancer: Understanding the Molecular Basis of Histologic Grade to Improve Prognosis", Journal of the National Cancer Institute, 2006, vol. 98, No. 4, p. 262-272.
Sparano J. et al. "TOP2A RNA expression and recurrence in estrogen receptor-positive breast cancer", Breast Cancer Research and Treatment, vol. 134, No. 2, 2012, pp. 751-757.
Van Wieringen et al. "Survival prediction using gene expression data: A review and comparison", Computational Statistics & Data Analysis, 2009, vol. 53, p. 1590-1603.
Van't Veer et al., "Gene expression profiling predicts clinical outcome of breast cancer," Nature, vol. 415, Jan. 31, 2002, pp. 530-536.
Waldron L. et al. "Optimized application of penalized regression methods to diverse genomic data", Bioinformatics, 2011, vol. 27, p. 3399-3406.
Wang Y. et al. "Gene-expression profiles to predict distant metastasis of lymph-node-negative primary breast cancer", Lancet, 2005, vol. 365, No. 9460, p. 671-679.

* cited by examiner

Figure 1B

| Gene Signature | Univariate Analysis HR (95% CI) | P-Value | Multivariable Analysis HR (95% CI) | P-Value |
|---|---|---|---|---|
| 20-gene SC signature | 2.72 (1.52-5.24) | 0.0005 | 2.89 (1.52-5.82) | 0.001 |
| 70-gene signature (van't Veer LJ et al.)* | 2.77 (1.41-5.43) | 0.0031 | 3.08 (1.48-6.41) | 0.0027 |
| 76-gene signature (Wang Y, et al.)* | 1.76 (0.92-3.34) | 0.086 | 1.9 (1.01-3.79) | 0.048 |
| Gene expression Grade Index (Sotiriou C, et al.)* | 2.41 (1.29-4.5) | 0.0059 | 2.93 (1.44-5.96) | 0.003 |

Figure 4A
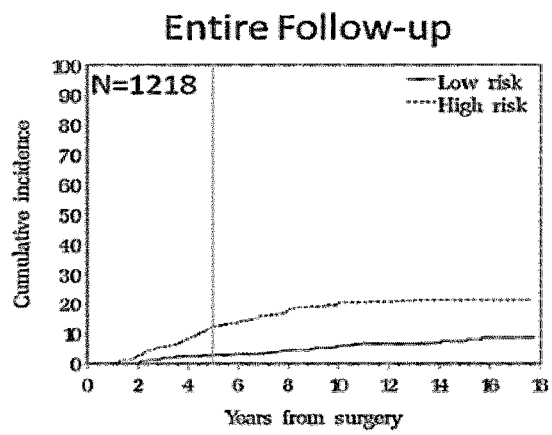
Figure 4B
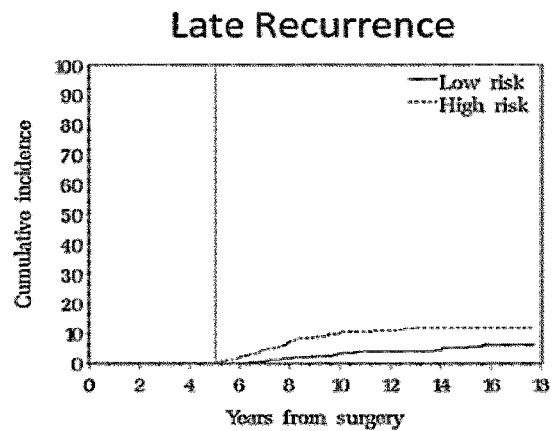
Figure 4C
| Time (years) | HR$_{\text{High vs. Low}}$ (95% CI) | P-value |
|---|---|---|
| 0 – 18 | 1.9 (1.3-2.7) | 0.0019 |
| 0 – 5 | 2.6 (1.5-4.4) | 0.0009 |
| 5 – 10 | 1.9 (1.0-3.3) | 0.0377 |

Figure 5A
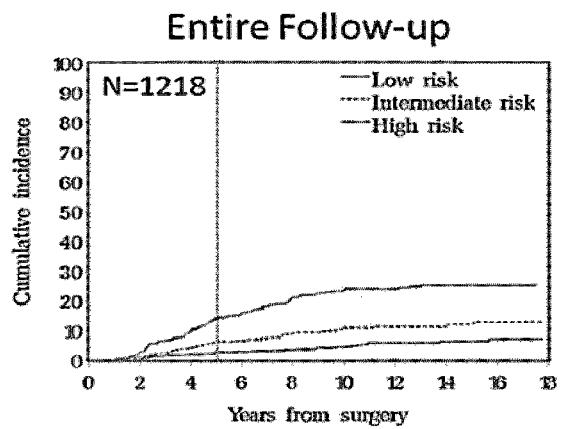
Figure 5B
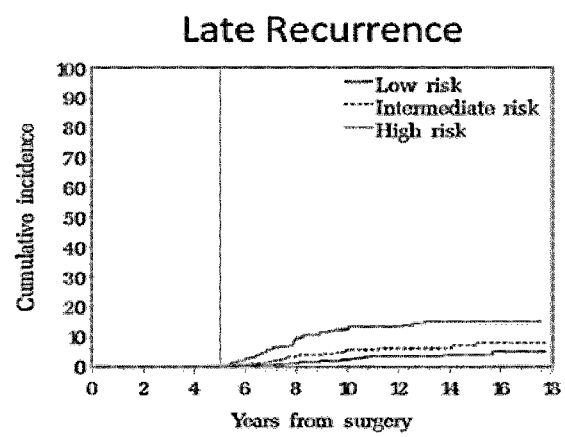
Figure 5C
| Time (years) | HR$_{\text{High vs. Low}}$ (95% CI) | P-value |
|---|---|---|
| 0 – 18 | 2.1 (1.3-3.6) | 0.0042 |
| 0 – 5 | 2.5 (1.3-5.2) | 0.0096 |
| 5 – 10 | 2.8 (1.2-6.4) | 0.0137 |

|  | C-index (95% CI) | p-value |
|---|---|---|
| Min C-Index | 0.69 (0.64-0.74) | 0.0411 |
| Max C-Index | 0.76 (0.72-0.81) | |

US 12,139,766 B2

METHODS AND KITS COMPRISING GENE SIGNATURES FOR STRATIFYING BREAST CANCER PATIENTS

RELATED APPLICATIONS

This application is a continuation of U.S. application Ser. No. 16/308,564, filed Dec. 10, 2018, now allowed, which is a U.S. National Phase application, filed under 35 U.S.C. § 371, of International Application number PCT/EP2017/064937, filed Jun. 19, 2017, which claims the benefit of and priority to European patent application no. 16175354.6, filed Jun. 20, 2016, and European patent application no. 16188855.7, filed Sep. 14, 2016. These documents are incorporated by reference herein in their entirety for all purposes.

INCORPORATION-BY-REFERENCE OF SEQUENCE LISTING

The Sequence Listing XML associated with this application is provided electronically in XML file format and is hereby incorporated by reference into the specification. The name of the XML file containing the Sequence Listing XML is "ACSC-001_C01US_SeqList.xml". The XML file is 56,735 bytes, created on Jul. 25, 2022, and is being submitted electronically via USPTO Patent Center.

FIELD OF THE INVENTION

This disclosure relates generally to the field of breast cancer biology, and specifically, to refined prognostic clinical tools, methods, and kits for the evaluation of risk and management of distant recurrence in ER+/HER2− breast cancer patients.

BACKGROUND OF THE INVENTION

Endocrine receptor-positive (ER+)/HER2-negative (HER2−) breast cancers constitute the majority of breast cancer cases. Due to the high level of molecular and clinical heterogeneity displayed by these cancers, prognosis and therapy response are often difficult to predict. This makes the clinical management of the ER+/HER2− breast cancer patients challenging, particularly, in terms of the type and the duration of the adjuvant systemic therapy an individual should receive. Based on the intrinsic risk of recurrence (typically assessed using standard clinico-pathological parameters), ER+/HER2− breast cancer patients may be offered adjuvant chemotherapy in addition to hormonal therapy or prolonged hormonal therapy beyond the five years standard of care. However, since standard clinico-pathological parameters are often insufficient to accurately predict risk of recurrence in these patients, a significant proportion of patients are, consequently, either over- or under-treated.

Accordingly, an unmet need exists for more refined prognostic clinical tools for the evaluation of risk and management of distant recurrence in ER+/HER2− breast cancer patients.

SUMMARY OF THE INVENTION

A need exists for refined prognostic clinical tools, methods, and kits for the evaluation of risk and management of distant recurrence in ER+/HER2− breast cancer patients.

One aspect of the present invention is a method for predicting a risk of breast cancer recurrence in a subject. The method comprises steps of (a) determining, in a sample, the expression of at least three genes from Table 3 or Table 9, wherein the at least three genes comprise at least EIF4EBP1, MRPS23, and TOP2A; and (b) calculating a risk score based upon the expression of the at least three genes.

Another aspect of the present invention is a method for stratifying a subject into a low or high risk group of breast cancer recurrence. The method comprises steps of (a) determining, in a sample, the expression of at least three genes from Table 3 or Table 9, wherein the at least three genes comprise at least EIF4EBP1, MRPS23, and TOP2A; (b) calculating a risk score based upon the expression of the at least three genes; and (c) stratifying the subject based upon the calculated risk score. In embodiments of this aspect, the subject who has a risk score greater than about the 2-class cut-off score as identified in Table 3 or Table 9 is stratified into a high risk group and the subject who has a risk score less than about the 2-class cut-off score as identified in Table 3 or Table 9 is stratified into a low risk group.

Yet another aspect of the present invention is a method for stratifying a subject into a low, intermediate, or high risk group of breast cancer recurrence. The method comprises steps of (a) determining, in a sample, the expression of at least three genes from Table 3 or Table 9, wherein the at least three genes comprise at least EIF4EBP1, MRPS23, and TOP2A; (b) calculating a risk score based upon the expression of the at least three genes; and (c) stratifying the subject based upon the calculated risk score. In embodiments of this aspect, the subject who has a risk score greater than about the 3-class cut-off score for the $66^{th}$ percentile as identified in Table 3 or Table 9 is stratified into a high risk group, the subject who has a risk score less than about the 3-class cut-off score for the $66^{th}$ percentile and greater than about the 3-class cut-off score for the $33^{rd}$ percentile as identified in Table 3 or Table 9 is stratified into an intermediate risk group, and the subject who has a risk score less than about the 3-class cut-off score for the $33^{rd}$ percentile as identified in Table 3 or Table 9 is stratified into a low risk group.

In embodiments of the above aspects, the subject stratified in a high risk group may be provided a cancer treatment that is more aggressive than the cancer treatment provided to the subject stratified in a low risk group. In embodiments, the subject stratified in a high risk group may be provided a cancer treatment that is more aggressive than the cancer treatment provided to the subject stratified in an intermediate risk group. In embodiments, the subject stratified in an intermediate risk group may be provided a cancer treatment that is more aggressive than the cancer treatment provided to the subject stratified in a low risk group.

An aspect is a method for treating a subject having a breast cancer. The method comprises steps of (a) determining, in a sample, the expression of at least three genes from Table 3 or Table 9, wherein the at least three genes comprise at least EIF4EBP1, MRPS23, and TOP2A; (b) calculating a risk score based upon the expression of the at least three genes; and (c) providing a cancer treatment to the subject. In embodiments of this aspect, the subject who has a risk score greater than about the 2-class cut-off score as identified in Table 3 or Table 9 may be provided a cancer treatment that is more aggressive than the cancer treatment provided to the subject who has a risk score less than about the 2-class cut-off score as identified in Table 3 or Table 9.

Yet another aspect is a method for treating a subject having a breast cancer. The method comprises steps of (a) determining, in a sample, the expression of at least three genes from Table 3 or Table 9, wherein the at least three genes comprise at least EIF4EBP1, MRPS23, and TOP2A; (b) calculating a risk score based upon the expression of the at least three genes; and (c) providing a cancer treatment to the subject. In embodiments of this aspect, the subject who has a risk score greater than about the 3-class cut-off score for the 66$^{th}$ percentile as identified in Table 3 or Table 9 may be provided a cancer treatment that is more aggressive than the cancer treatment provided to the subject who has a risk score less than about the 3-class cut-off score for the 66$^{th}$ percentile as identified in Table 3 or Table 9; and wherein the subject who has a risk score less than about the 3-class cut-off score for the 66$^{th}$ percentile as identified in Table 3 or Table 9 and greater than about the 33$^{rd}$ percentile as identified in Table 3 or Table 9 may be provided a cancer treatment that is more aggressive than the cancer treatment provided to the subject who has a risk score less than about the 3-class cut-off score for the 33$^{rd}$ percentile as identified in Table 3 or Table 9.

In any of the above aspects or embodiments, the at least three genes may consist of EIF4EBP1, MRPS23, and TOP2A. In any of the above aspects or embodiments, the at least three genes may comprise at least APOBEC3B, CENPW, EIF4EBP1, EXOSC4, LY6E, MMP1, MRPS23, NDUFB10, and TOP2A. In any of the above aspects or embodiments, the at least three genes may consist of APOBEC3B, CENPW, EIF4EBP1, EXOSC4, LY6E, MMP1, MRPS23, NDUFB10, and TOP2A. In any of the above aspects or embodiments, the at least three genes may comprise at least ALYREF, APOBEC3B, CDK1, CENPW, EIF4EBP1, EXOSC4, H2AFJ, LY6E, MIEN1, MMP1, MRPS23, NDUFB10, NOL3, RACGAP1, SFN, and TOP2A. In any of the above aspects or embodiments, the at least three genes may consist of ALYREF, APOBEC3B, CDK1, CENPW, EIF4EBP1, EXOSC4, H2AFJ, LY6E, MIEN1, MMP1, MRPS23, NDUFB10, NOL3, RACGAP1, SFN, and TOP2A. In any of the above aspects or embodiments, the at least three genes may consist of each gene from Table 3 or Table 9 and wherein each cut-off score is as identified in Table 3.

In any of the above aspects or embodiments, the risk score is calculated according to the following formula:

$$\text{Risk score} = \Sigma_i(\beta_i * Cq_{normalized}),$$

wherein i is the summation index for the at least three genes; p is the ridge penalized Cox model coefficient for each of the at least three genes; and $Cq_{normalized}$ is the normalized average Cq for each of the at least three genes.

Other risk models and formulae may be derived from the disclosure recited herein.

In any of the above aspects or embodiments, $Cq_{normalized}$ is normalized to the expression of at least one reference gene; in embodiments the at least one reference gene is a housekeeping gene, e.g., as recited herein. In any of the above aspects or embodiments, $Cq_{normalized}$ is normalized to the expression of at least one reference gene (e.g., all four genes) selected from the group consisting of GAPDH, GUSB, HPRT1, and TBP. $Cq_{normalized}$ may be calculated according to the following formula: $Cq_{normalized}$=AVG Cq−SF, in which wherein SF is the difference between the AVG Cq value of the at least one reference gene for each subject and a constant reference value K, wherein K=25.012586069, which represents the mean of the AVG Cq of the at least one reference gene calculated across a plurality of training samples.

In any of the above aspects or embodiments, the gene expression may be determined using any method known in the art. Preferably, the gene expression may be determined using one or more techniques selected from the group consisting of analysis of single strand conformation polymorphism, capillary electrophoresis, denaturing high performance liquid chromatography, digital molecular barcoding technology, e.g., Nanostring's nCounter® system, direct sequencing, DNA mismatch-binding protein assays, dynamic allele-specific hybridization, Fluorescent in situ hybridization (FISH), high-density oligonucleotide SNP arrays, high-resolution melting analysis, microarray, next generation sequencing (NGS), e.g., using the Illumina Genome Analyzer, ABI Solid instrument, Roche 454 instrument, Heliscope instrument, Northern blot analysis, nuclease protection analysis, oligonucleotide ligase assays, polymerase chain reaction (PCR), primer extension assays, Quantigene analysis, quantitative nuclease-protection assay (qNPA), reporter gene detection, restriction fragment length polymorphism (RFLP) assays, reverse transcription and real-time quantitative polymerase chain reaction (RT-qPCR), reverse transcription-polymerase chain reaction (RT-PCR), RNA sequencing (RNA-seq), Serial analysis of gene expression (SAGE), Single Molecule Real Time (SMRT) DNA sequencing technology, SNPLex, Southern blot analysis, Sybr Green chemistry, TaqMan-based assays, temperature gradient gel electrophoresis (TGGE), Tiling array, Western blot analysis, and immunohistochemistry. In any of the above aspects or embodiments, the gene expression may be determined using reverse transcription and real-time quantitative polymerase chain reaction (RT-qPCR) with primers and/or probes (e.g., TaqMan® probes) specific for each of said at least three genes. Alternately, the gene expression may be determined using microarray analysis with probes specific for an expression product of each of said at least three genes.

In any of the above aspects or embodiments, the sample may be obtained from the subject. The sample may be a tumor obtained from the subject, a cancerous cell obtained from the subject, or a cancer stem cell obtained from the subject. The sample may be a primary cell line derived from a tumor obtained from the subject, from a cancerous cell obtained from the subject, or from a cancer stem cell obtained from the subject.

In any of the above aspects or embodiments, minimum and maximum risk scores from a training set (as described below) were used to scale risk scores in a 0-1 range.

In any of the above aspects or embodiments, the subject has an ER+/HER2− breast cancer.

Another aspect of the present invention is a kit for use in the method of any of the above aspects or embodiments. The kit may comprise reagents sufficient for determining the expression levels of the at least three genes.

Any of the above aspects and embodiments can be combined with any other aspect or embodiment as disclosed here in the Summary and/or in the Detailed Description sections, including the below Examples.

Other features and advantages of the invention will be apparent from the following detailed description and claims.

BRIEF DESCRIPTION OF THE DRAWINGS

The above and further features will be more clearly appreciated from the following detailed description when taken in conjunction with the accompanying drawings.

FIGS. 1A and 1B. Validation of the 20-gene SC signature by in silico meta-analysis of publicly available breast cancer gene expression datasets. FIG. 1A. Clustering analysis of the expression of the 20 genes and their prognostic significance determined by Kaplan-Meier analysis (DMFS: distant metastasis-free survival) in independent breast cancer datasets. Hazard ratio (HR) of univariate analysis, 95% confidence intervals (CI) and p-values (P) are indicated. FIG. 1B. Comparison of the predictive power for DMFS of the 20-gene SC signature with published gene signatures [70-gene (van't Veer L J et al. 2002. Nature 415:530), 76-gene (Wang Y, et al. 2005. Lancet 365:671) and Gene expression Grade Index (Sotiriou C, et al. 2006. JNCI 98:262.)] at >20 years of follow-up in individual patients of the TRANSBIG study by univariate and multivariable (adjusted for age, tumor size, ER status and tumor grade) analysis. P, p-value for the difference in HRs between gene signature-positive vs. gene signature-negative patients calculated for each gene signature analyzed. *Data from Haibe-Kains B., 2008. BMC Genomics 9:394.

FIGS. 4A to 4C. The 2-class StemPrintER20 risk model predicts both early (0-5 years) and late (5-10 years) recurrence in the ER+/HER2− validation set (N=1,218) of the IEO cohort. The cumulative incidence of distant metastasis over the entire follow-up period (FIG. 4A) and from 5 years after surgery (FIG. 4B) are shown. FIG. 4C: Hazard ratios (HR) for the high-risk group relative to the low-risk group (HRHigh vs. Low) for the indicated time intervals were calculated based on a multivariable analysis adjusted for pT, pN, tumor grade, Ki-67 and age.

FIGS. 5A to 5C. The 3-class StemPrintER20 risk model predicts both early (0-5 years) and late (5-10 years) recurrence in the ER+/HER2− validation set (N=1,218) of the IEO cohort. The cumulative incidence of distant metastasis over the entire follow-up period (FIG. 5A) and from 5 years after surgery (FIG. 5B) are shown. FIG. 5C: Hazard ratios (HR) for the high-risk group relative to the low-risk group (HRHigh vs. Low) for the indicated time intervals were calculated based on a multivariable analysis adjusted for pT, pN, tumor grade, Ki-67 and age.

FIG. 6A, representation of the distribution of the C-index values associated with the 15,000 models derived from the 1,000 simulations performed for each of the 15 different training sets. Each line represents a different training set: blue lines=one-third as training; red lines=two-thirds as training; black line=entire cohort; violet line=training set used for the development of StemPrintER20; orange line=validation set used for the development of StemPrintER20. FIG. 6B, statistical analysis of the variation between the minimal and maximum C-index, indicated together with their confidence intervals (CI). This difference is not statistically significant considering a stringent p-value of 0.01.

FIGS. 7A and 7B. Identification of the TOP3, TOP9 and TOP16 clusters. FIG. 7A, analysis of the frequency of occurrence of the 20 stem cell genes, each considered individually, in the indicated number of simulations performed using datasets based on a one-third (33%) or a two-third (66%) split, or based on the entire cohort. A cut-off of 80% was used to select the minimal cluster of genes in each split. This approach identified a set of 3 most represented genes (TOP3) from the 7,000 simulations of the one-third training set, nine most represented genes from the 7,000 simulations of the two-thirds training set, and 16 most represented genes from the 1,000 simulations of the training set based on the entire cohort. FIG. 7B, frequency of occurrence of the TOP3, TOP9 and TOP16 signatures, as a whole, in the respective datasets.

DETAILED DESCRIPTION OF THE INVENTION

Figure 1A:
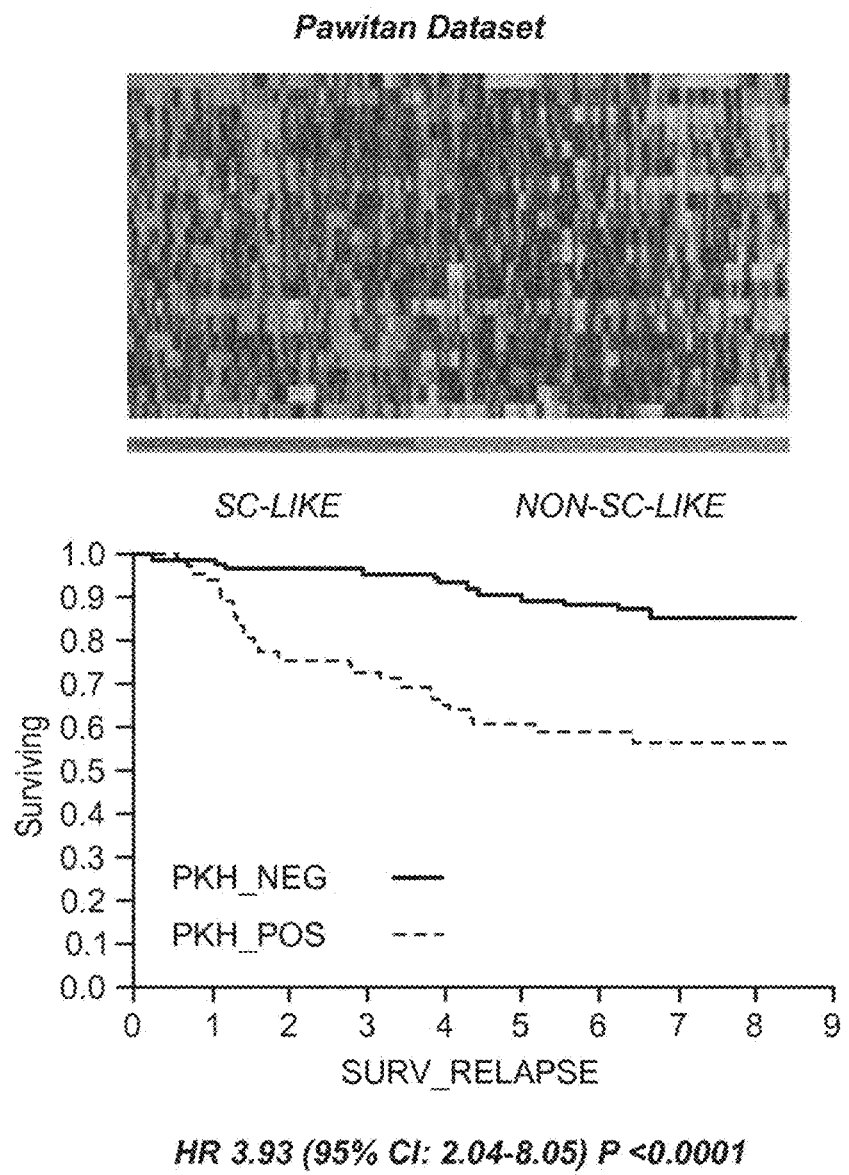
Figure 1A:
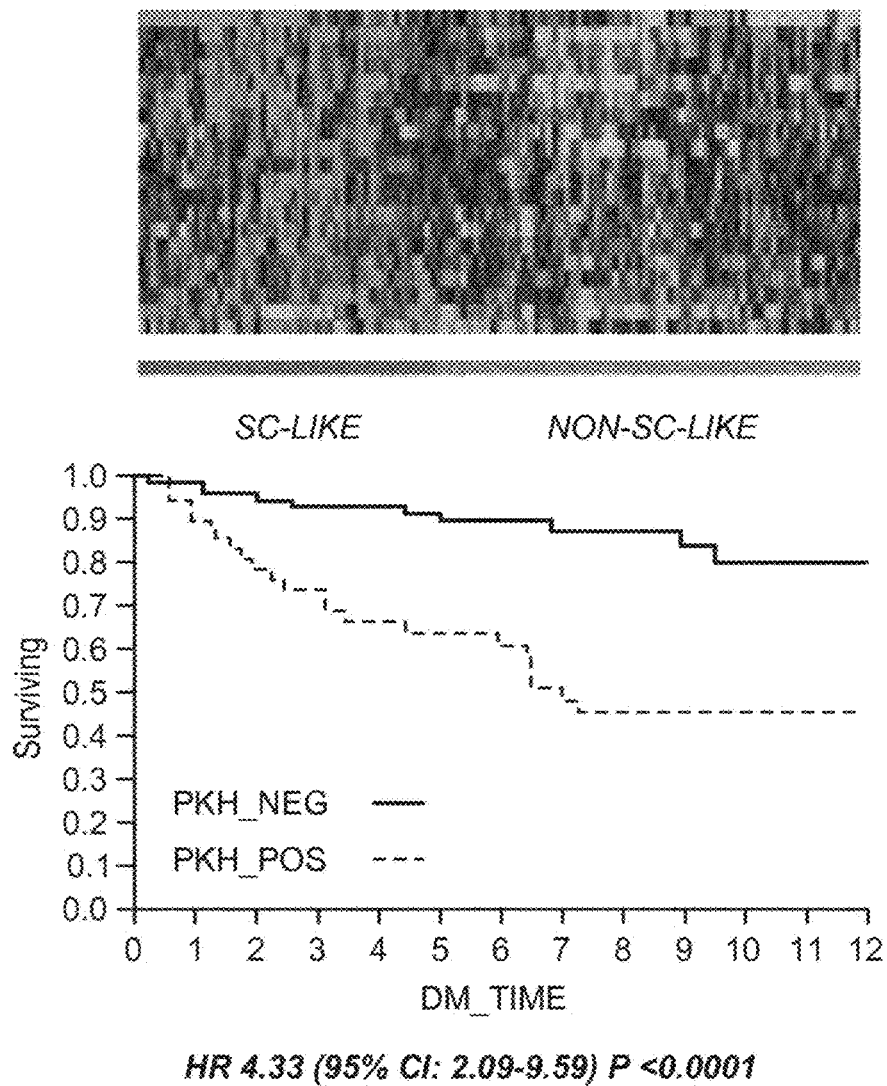
Figure 1A:
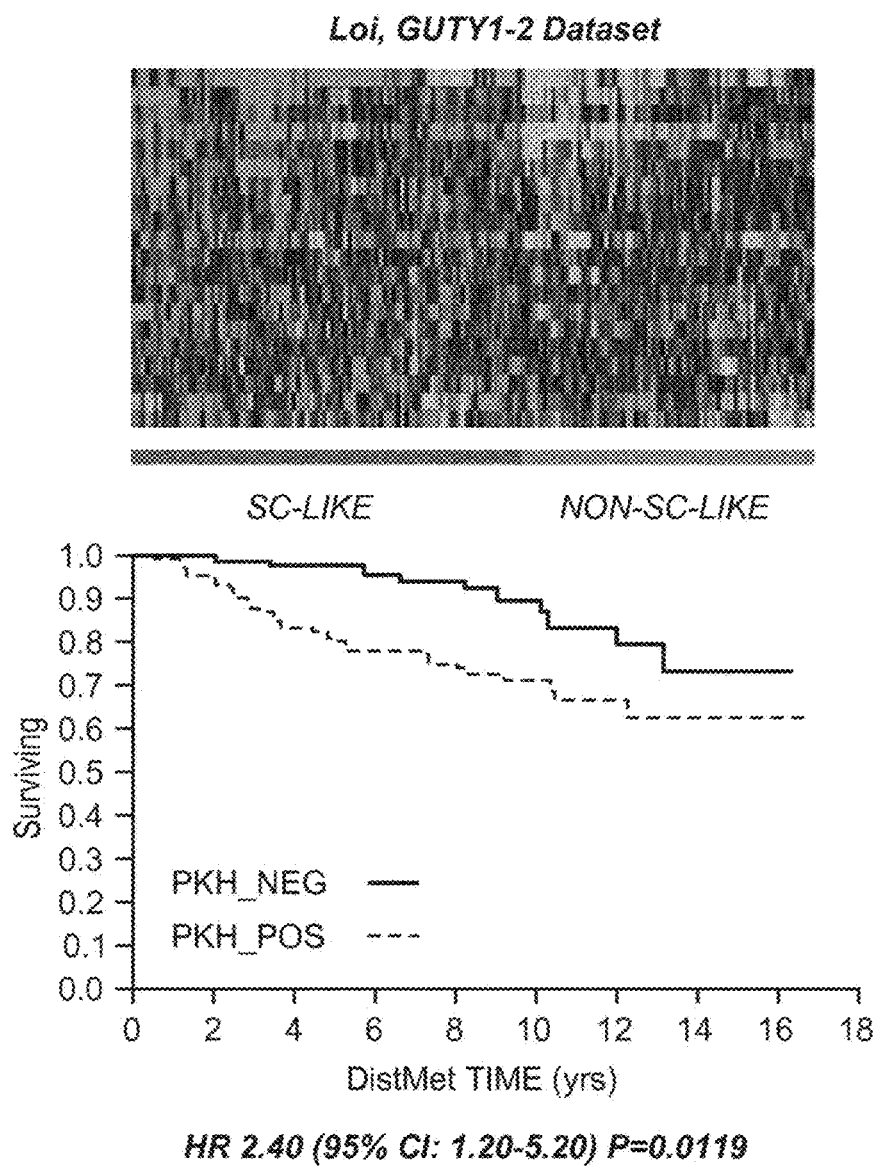

The present invention relates to refined prognostic clinical tools, methods, and kits for the evaluation of risk and management of distant recurrence in ER+/HER2− breast cancer patients.

The present invention is based in part through a retrospective analysis of a consecutive cohort of 1,827 ER+/HER2− breast cancer patients with long-term follow-up (~15 years), a 20-gene signature was established that is able to stratify breast cancer patients according to risk of early and late recurrence. Thus, the "StemPrintER20 genomic predictor" functions as a prognostic-predictive clinical tool in ER+/HER2− breast cancer patients that may be used to guide clinical decision-making on the selection of adjuvant systemic therapies. Furthermore, the 20-gene signature was further partitioned into 3, 5, 9, and 16-gene signatures, i.e., the "StemPrintER3 genomic predictor", "StemPrintER5 genomic predictor", "StemPrintER9 genomic predictor", and "StemPrintER16 genomic predictor", which function as prognostic-predictive clinical tools in ER+/HER2− breast cancer patients that may be used to guide clinical decision-making on the selection of adjuvant systemic therapies.

One aspect of the present invention is a method for predicting a risk of breast cancer recurrence in a subject. The method comprises steps of (a) determining, in a sample the expression of at least three genes from Table 3 or Table 9, wherein the at least three genes comprise at least EIF4EBP1, MRPS23, and TOP2A; and (b) calculating a risk score according to the following formula: Risk score=$\Sigma_i(\beta_i*Cq_{normalized})$, in which i is the summation index for the at least three genes; p is the ridge penalized Cox model coefficient for each of the at least three genes; and $Cq_{normalized}$ is the normalized average Cq for each of the at least three genes.

Another aspect of the present invention is a method for stratifying a subject into a low or high risk group of breast cancer recurrence. The method comprises steps of (a) determining, in a sample the expression of at least three genes from Table 3 or Table 9, wherein the at least three genes comprise at least EIF4EBP1, MRPS23, and TOP2A; and (b) calculating a risk score according to the following formula: Risk score=$\Sigma_i(\beta_i*Cq_{normalized})$, in which i is the summation index for the at least three genes; p is the ridge penalized Cox model coefficient for each of the at least three genes; and $Cq_{normalized}$ is the normalized average Cq for each of the at least three genes. In this aspect, the subject who has a risk score greater than about the 2-class cut-off score as identified in Table 3 or Table 9 is stratified into a high risk group and the subject who has a risk score less than about the 2-class cut-off score as identified in Table 3 or Table 9 is stratified into a low risk group.

Yet another aspect of the present invention is a method for stratifying a subject into a low, intermediate, or high risk group of breast cancer recurrence. The method comprises steps of (a) determining, in a sample the expression of at least three genes from Table 3 or Table 9, wherein the at least three genes comprise at least EIF4EBP1, MRPS23, and TOP2A; and (b) calculating a risk score according to the following formula: Risk score=$\Sigma_i(\beta_i*Cq_{normalized})$, in which i is the summation index for the at least three genes; P is the ridge penalized Cox model coefficient for each of the at least three genes; and $Cq_{normalized}$ is the normalized average Cq for each of the at least three genes. In this aspect, the subject who has a risk score greater than about the 3-class cut-off score for the $66^{th}$ percentile as identified in Table 3 or Table 9 is stratified into a high risk group, the subject who has a risk score less than about the 3-class cut-off score for the $66^{th}$ percentile and greater than about the 3-class cut-off score for the $33^{rd}$ percentile as identified in Table 3 or Table 9 is stratified into an intermediate risk group, and the subject who has a risk score less than about the 3-class cut-off score for the $33^{rd}$ percentile as identified in Table 3 or Table 9 is stratified into a low risk group.

In embodiments of the above aspects, the subject stratified in a high risk group may be provided a cancer treatment that is more aggressive than the cancer treatment provided to the subject stratified in a low risk group. In embodiments, the subject stratified in a high risk group may be provided a cancer treatment that is more aggressive than the cancer treatment provided to the subject stratified in an intermediate risk group. In embodiments, the subject stratified in an intermediate risk group may be provided a cancer treatment that is more aggressive than the cancer treatment provided to the subject stratified in a low risk group.

Stratification of subjects into risk groups may be influenced by other features of the subject. For example, risk models can also be derived. As examples, categorizations may be more appropriate for subsets of patients (e.g., pre-post-menopausal or NO N+, treatments).

An aspect is a method for treating a subject having a breast cancer. The method comprises steps of (a) determining, in a sample the expression of at least three genes from Table 3 or Table 9, wherein the at least three genes comprise at least EIF4EBP1, MRPS23, and TOP2A; (b) calculating a risk score according to the following formula: Risk score=$\Sigma_i(\beta_i*Cq_{normalized})$; in which i is the summation index for the at least three genes; p is the ridge penalized Cox model coefficient for each of the at least three genes; and $Cq_{normalized}$ is the normalized average Cq for each of the at least three genes; and (c) providing a cancer treatment to the subject. In this aspect, the subject who has a risk score greater than about the 2-class cut-off score as identified in Table 3 or Table 9 may be provided a cancer treatment that is more aggressive than the cancer treatment provided to the subject who has a risk score less than about the 2-class cut-off score as identified in Table 3 or Table 9.

Yet another aspect is a method for treating a subject having a breast cancer. The method comprises steps of (a) determining, in a sample the expression of at least three genes from Table 3 or Table 9, wherein the at least three genes comprise at least EIF4EBP1, MRPS23, and TOP2A; (b) calculating a risk score according to the following formula: Risk score=$\Sigma_i(\beta_i* Cq_{normalized})$, in which i is the summation index for the at least three genes; p is the ridge penalized Cox model coefficient for each of the at least three genes; and $Cq_{normalized}$ is the normalized average Cq for each of the at least three genes; and (c) providing a cancer treatment to the subject. In this aspect, the subject who has a risk score greater than about the 3-class cut-off score for the $66^{th}$ percentile as identified in Table 3 or Table 9 may be provided a cancer treatment that is more aggressive than the cancer treatment provided to the subject who has a risk score less than about the 3-class cut-off score for the $66^{th}$ percentile as identified in Table 3 or Table 9; and wherein the subject who has a risk score less than about the 3-class cut-off score for the $66^{th}$ percentile as identified in Table 3 or Table 9 and greater than about the $33^{rd}$ percentile as identified in Table 3 or Table 9 may be provided a cancer treatment that is more aggressive than the cancer treatment provided to the subject who has a risk score less than about the 3-class cut-off score for the $33^{rd}$ percentile as identified in Table 3 or Table 9.

In any of the above aspects or embodiments, the at least three genes may consist of EIF4EBP1, MRPS23, and TOP2A. In any of the above aspects or embodiments, the at least three genes may comprise at least APOBEC3B, CENPW, EIF4EBP1, EXOSC4, LY6E, MMP1, MRPS23, NDUFB10, and TOP2A. In any of the above aspects or embodiments, the at least three genes may consist of APOBEC3B, CENPW, EIF4EBP1, EXOSC4, LY6E, MMP1, MRPS23, NDUFB10, and TOP2A. In any of the above aspects or embodiments, the at least three genes may comprise at least ALYREF, APOBEC3B, CDK1, CENPW, EIF4EBP1, EXOSC4, H2AFJ, LY6E, MIEN1, MMP1, MRPS23, NDUFB10, NOL3, RACGAP1, SFN, and TOP2A. In any of the above aspects or embodiments, the at least three genes may consist of ALYREF, APOBEC3B, CDK1, CENPW, EIF4EBP1, EXOSC4, H2AFJ, LY6E, MIEN1, MMP1, MRPS23, NDUFB10, NOL3, RACGAP1, SFN, and TOP2A. In any of the above aspects or embodiments, the at least three genes may consist of each gene from Table 3 or Table 9 and wherein each cut-off score is as identified in Table 3.

In any of the above aspects or embodiments, $Cq_{normalized}$ is normalized to the expression of at least one reference gene; in embodiments the at least one referenced gene is a housekeeping gene, e.g., as recited herein. In any of the above aspects or embodiments, $Cq_{normalized}$ is normalized to the expression of at least one reference gene (e.g., all four genes) selected from the group consisting of GAPDH, GUSB, HPRT1, and TBP. $Cq_{normalized}$ may be calculated according to the following formula: Cqnormaized=AVG Cq–SF, in which wherein SF is the difference between the AVG Cq value of the reference genes for each subject and a constant reference value K, wherein K=25.012586069, which represents the mean of the AVG Cq of the four reference genes calculated across a plurality of training samples.

Other risk models and formulae may be derived from the disclosure recited herein.

In particular embodiments the methods comprise collecting a sample, e.g., "a biological sample," comprising a cancer cell or cancerous tissue, such as a breast tissue sample comprising a cancerous cell and/or a cancer stem cell or a primary breast tumor tissue sample. By "biological sample" is intended any sampling of cells, tissues, or bodily fluids in which expression of a breast cancer, stem cell, or stem cell-like gene can be detected. Examples of such biological samples include, but are not limited to, biopsies and smears. Bodily fluids may be useful in the present disclosure and include blood, lymph, urine, saliva, nipple aspirates, gynecological fluids, or any other bodily secretion or derivative thereof when the bodily fluid comprises a cancerous cell and/or a cancer stem cell. Blood can include whole blood, plasma, serum, or any derivative of blood. In some embodiments, the biological sample includes breast cancer cells, particularly breast tissue from a biopsy, such as a breast tumor tissue sample, and any derivate thereof, such as three-dimensional structures generated in organotypic cultures in matrices or in suspension cultures (commonly regarded as to mammospheres). Biological samples may be obtained from a subject by a variety of techniques including, for example, by scraping or swabbing an area, by using a needle to aspirate cells or bodily fluids, or by removing a tissue sample (i.e., biopsy). Methods for collecting various biological samples are well known in the art. In some embodiments, a breast tissue sample is obtained by, for example, fine needle aspiration biopsy, core needle biopsy, or excisional biopsy. Fixative and staining solutions may be applied to the cells or tissues for preserving the specimen and for facilitating examination. Biological samples, particularly breast tissue samples, may be transferred to a glass slide for viewing under magnification. In one embodiment, the biological sample is a formalin-fixed, paraffin-embedded breast tissue sample, particularly a primary breast tumor sample or a cancerous cell. In various embodiments, the tissue sample is obtained from a pathologist-guided tissue core sample. In various embodiments, the tissue sample is a "fresh", i.e., unfixed and/or unfrozen tissue samples (e.g., obtained from a biopsy). In various embodiments, the tissue sample is a frozen, unfixed tissue sample.

In any of the above aspects or embodiments, the sample may be obtained from the subject. The sample may be a tumor obtained from the subject, a cancerous cell obtained from the subject, or a cancer stem cell obtained from the subject. The sample may be a primary cell line derived from a tumor obtained from the subject, from a cancerous cell obtained from the subject, or from a cancer stem cell obtained from the subject.

Breast cancer includes all forms of cancer of the breast. Breast cancer can include primary epithelial breast cancers and any derivate thereof, such as three-dimensional structures generated in organotypic cultures in matrices or in suspension cultures (commonly regarded as to mammospheres). Breast cancer can include cancers in which the mammary tissue breast is involved. Breast cancer can include Stage I, II, IIIA, IIIB, IIIC and IV breast cancer. Ductal carcinoma of the breast can include invasive carcinoma, invasive carcinoma in situ with predominant intraductal component, inflammatory breast cancer, and a ductal carcinoma of the breast with a histologic type selected from the group consisting of comedo, mucinous (colloid), medullary, medullary with lymphocytic infiltrate, papillary, scirrhous, and tubular. Lobular carcinoma of the breast can include invasive lobular carcinoma with predominant in situ component, invasive lobular carcinoma, and infiltrating lobular carcinoma. Breast cancer can include Paget's disease, Paget's disease with intraductal carcinoma, and Paget's disease with invasive ductal carcinoma. Breast cancer can include breast neoplasms having histologic and ultrastructual heterogeneity (e.g., mixed cell types). A breast cancer that is relevant to the present invention may include familial and hereditary breast cancer.

A breast cancer relevant to the present invention (e.g., that is treated) can include a localized tumor of the breast. A breast cancer can include a tumor of the breast that is associated with a negative sentinel lymph node (SLN) biopsy. A breast cancer can include a tumor of the breast that is associated with a positive sentinel lymph node (SLN) biopsy. A breast cancer can include a tumor of the breast that is associated with one or more positive axillary lymph nodes, where the axillary lymph nodes have been staged by any applicable method. A breast cancer can include a tumor of the breast that has been typed as having nodal negative status (e.g., node-negative) or nodal positive status (e.g., node-positive). A breast cancer can include a tumor of the breast that has been typed as being hormone receptor negative (e.g., estrogen receptor-negative) or hormone receptor status (e.g., estrogen receptor-positive or estrogen receptor-negative). A breast cancer can include a tumor of the breast that has metastasized to other locations in the body. A breast cancer can be classified as having metastasized to a location selected from the group consisting of bone, lung, liver, lymph nodes, and brain. A breast cancer can be classified according to a characteristic selected from the group consisting of metastatic, localized, regional, local-regional, locally advanced, distant, multicentric, bilateral, ipsilateral, contralateral, newly diagnosed, recurrent, and inoperable.

As used herein, a "subject in need thereof" is a subject having breast cancer or presenting with one or more symptoms of breast cancer, a subject suspected of having breast cancer, a subject having undiagnosed breast cancer, or a subject actually diagnosed with breast cancer. Preferably, a subject in need thereof has a diagnosed breast cancer. The breast cancer can be primary breast cancer, locally advanced breast cancer or metastatic breast cancer. A "subject" includes a mammal. The mammal can be any mammal, e.g., a human, a primate, a mouse, a rat, a dog, a cat, a cow, a horse, a goat, a camel, a sheep and a pig. Preferably, the subject is human. The subject may be a male or a female. The subject may have been diagnosed by a skilled artisan as having a breast cancer and is included in a subpopulation of humans who currently have breast cancer or had breast cancer. The subject that has breast cancer may be pre-mastectomy or post-mastectomy.

The methods of the present invention can include determining at least one of, a combination of, or each of, the following: tumor size (pT), tumor grade, nodal status/nodal involvement (pN), intrinsic subtype, histological type, perivascular infiltration, Ki-67 status, estrogen receptor (ER) status, progesterone receptor (PgR) status, and/or HER2/ERBB2 status.

Any method available in the art for detecting gene expression of the breast cancer, stem cell, or stem cell-like genes is encompassed herein. By "detecting expression" is intended determining the quantity or presence of an RNA transcript or its expression product of a gene. Non-limiting examples of methods for detecting gene expression include but are not limited to analysis of single strand conformation polymorphism, capillary electrophoresis, denaturing high performance liquid chromatography, digital molecular barcoding technology, e.g., Nanostring's nCounter® system, direct sequencing, DNA mismatch-binding protein assays, dynamic allele-specific hybridization, Fluorescent in situ hybridization (FISH), high-density oligonucleotide SNP arrays, high-resolution melting analysis, microarray, next generation sequencing (NGS), e.g., using the Illumina Genome Analyzer, ABI Solid instrument, Roche 454 instrument, Heliscope instrument, Northern blot analysis, nuclease protection analysis, oligonucleotide ligase assays, polymerase chain reaction (PCR), primer extension assays, Quantigene analysis, quantitative nuclease-protection assay (qNPA), reporter gene detection, restriction fragment length polymorphism (RFLP) assays, reverse transcription and real-time quantitative polymerase chain reaction (RT-qPCR), reverse transcription-polymerase chain reaction (RT-PCR), RNA sequencing (RNA-seq), Serial analysis of gene expression (SAGE), Single Molecule Real Time (SMRT) DNA sequencing technology, SNPLex, Southern blot analysis, Sybr Green chemistry, TaqMan-based assays, temperature gradient gel electrophoresis (TGGE), Tiling array, Western blot analysis, and immunohistochemistry.

Methods for detecting expression of the genes of the disclosure, that is, gene expression profiling, include methods based on hybridization analysis of polynucleotides, methods based on sequencing of polynucleotides, immunohistochemistry methods, and proteomics-based methods. In preferred embodiments, PCR-based methods, such as reverse transcription PCR (RT-PCR) (Weis et al., TIG 8:263-64, 1992), and array-based methods such as microarray (Schena et al., Science 270:467-70, 1995) are used. By "microarray" is intended an ordered arrangement of hybridizable array elements, such as, for example, polynucleotide probes, on a substrate. The term "probe" refers to any molecule that is capable of selectively binding to a specifically intended target biomolecule, for example, a nucleotide transcript or a protein encoded by or corresponding to an intrinsic gene. Probes can be synthesized by one of skill in the art, or derived from appropriate biological preparations. Probes may be specifically designed to be labeled. Examples of molecules that can be utilized as probes include, but are not limited to, RNA, DNA, proteins, antibodies, and organic molecules.

Many expression detection methods use isolated RNA. The starting material is typically total RNA isolated from a biological sample, such as a tumor or cell line derived from a tumor (i.e., a primary cell line), and corresponding normal tissue or cell line (e.g., which may serve as a control), respectively. If the source of RNA is a primary tumor, RNA (e.g., mRNA) can be extracted, for example, from frozen or archived paraffin-embedded and fixed (e.g., formalin-fixed) tissue samples (e.g., pathologist-guided tissue core samples) and "fresh", i.e., unfixed and/or unfrozen tissue samples (e.g., obtained from a biopsy).

General methods for RNA extraction are well known in the art and are disclosed in standard textbooks of molecular biology, including Ausubel et al., ed., Current Protocols in Molecular Biology, John Wiley & Sons, New York 1987-1999. Methods for RNA extraction from paraffin embedded tissues are disclosed, for example, in Rupp and Locker, Lab Invest. 56:A67, (1987); and De Andres et al. Biotechniques 18:42-44, (1995). In particular, RNA isolation can be performed using a purification kit, a buffer set and protease from commercial manufacturers, such as Qiagen (Valencia, CA), according to the manufacturer's instructions. For example, total RNA from cells in culture can be isolated using Qiagen RNeasy mini-columns. Other commercially available RNA isolation kits include MASTERPURE™ Complete DNA and RNA Purification Kit (Epicentre, Madison, Wis.) and Paraffin Block RNA Isolation Kit (Ambion, Austin, TX). Total RNA from tissue samples can be isolated, for example, using RNA Stat-60 (Tel-Test, Friendswood, TX). Total RNA from FFPE can be isolated, for example, using High Pure FFPE RNA Microkit, Cat No. 04823125001 (Roche Applied Science, Indianapolis, IN). RNA prepared from a tumor can be isolated, for example, by cesium chloride density gradient centrifligation. Additionally, large numbers of tissue samples can readily be processed using techniques well known to those of skill in the art, such as, for example, the single-step RNA isolation process of Chomczynski (U.S. Pat. No. 4,843,155).

A preferred method for determining the level of gene expression in a sample involves the process of nucleic acid amplification, for example, by RT-PCR (U.S. Pat. No. 4,683,202), ligase chain reaction (Barany, PNAS USA 88: 189-93, (1991)), self-sustained sequence replication (Guatelli et al., Proc. Natl. Acad. Sci USA 87: 1874-78, (1990)), transcriptional amplification system (Kwoh et al., Proc. Natl. Acad. Sci USA 86: 1173-77, (1989)), Q-Beta Replicase (Lizardi et al., Bio/Technology 6:1197, (1988)), rolling circle replication (U.S. Pat. No. 5,854,033), or any other nucleic acid amplification method, followed by the detection of the amplified molecules using techniques well known to those of skill in the art. These detection schemes are especially useful for the detection of nucleic acid molecules if such molecules are present in very low numbers.

In particular aspects of the disclosure, intrinsic gene expression is assessed by quantitative RT-PCR. Numerous different PCR or QPCR protocols are known in the art and exemplified herein below and can be directly applied or adapted for use using the presently-described compositions for the detection and/or quantification of the genes listed herein. Generally, in PCR, a target polynucleotide sequence is amplified by reaction with at least one oligonucleotide primer or pair of oligonucleotide primers. The primer(s) hybridize to a complementary region of the target nucleic acid and a DNA polymerase extends the primer(s) to amplify the target sequence. Under conditions sufficient to provide polymerase-based nucleic acid amplification products, a nucleic acid fragment of one size dominates the reaction products (the target polynucleotide sequence which is the amplification product). The amplification cycle is repeated to increase the concentration of the single target polynucleotide sequence. The reaction can be performed in any thermocycler commonly used for PCR. However, preferred are cyclers with real time fluorescence measurement capabilities, for example, SMARTCYCLER® (Cepheid, Sunnyvale, CA), ABI PRISM 7700® (Applied Biosystems, Foster City, Calif.), ROTOR-GENE™ (Corbett Research, Sydney, Australia), LIGHTCYCLER® (Roche Diagnostics Corp, Indianapolis, Ind.), ICYCLER® (Biorad Laboratories, Hercules, Calif.) and MX4000® (Stratagene, La Jolla, Calif.).

In another embodiment of the disclosure, microarrays are used for expression profiling. Microarrays are particularly well suited for this purpose because of the reproducibility between different experiments. DNA microarrays provide one method for the simultaneous measurement of the expression levels of large numbers of genes. Each array consists of a reproducible pattern of capture probes attached to a solid support. Labeled RNA or DNA is hybridized to complementary probes on the array and then detected by laser scanning. Hybridization intensities for each probe on the array are determined and converted to a quantitative value representing relative gene expression levels. See, for example, U.S. Pat. Nos. 6,040,138, 5,800,992 and 6,020,135, 6,033,860, and 6,344,316. High-density oligonucleotide arrays are particularly useful for determining the gene expression for a large number of RNAs in a sample.

In methods of the present invention, gene expression is normalized to the expression of at least one reference gene. The at least one reference gene may be a housekeeping gene. Exemplary housekeeping genes include and are not limited to AAAS, AAGAB, AAMP, AAR2, AARS, AARS2, AARSD1, AASDHPPT, AATF, ABCB10, ABCB7, ABCD3, ABCE1, ABCF1, ABCF2, ABCF3, ABHD10, ABHD12, ABHD13, ABHD14A, ABHD16A, ABHD4, ABHD8, ABI1, ABT1, ACAD9, ACADVL, ACAP3, ACBD3, ACBD5, ACBD6, ACIN1, ACLY, ACOT13, ACOT8, ACOT9, ACOX1, ACOX3, ACP1, ACSF3, ACSL3, ACSS2, ACTR10, ACTR1A, ACTR1B, ACTR5, ACTR8, ACVR1, ACVR1B, ADCK2, ADCK4, ADH5, ADI1, ADIPOR1, ADIPOR2, ADK, ADNP, ADO, ADPRH, ADPRHL2, ADPRM, ADSL, AES, AFF4, AFTPH, AGFG1, AGGF1, AGPAT1, AGPAT3, AGPAT6, AGPS, AHCY, AHSA1, AIMP1, AIP, AK2, AK3, AKAP8, AKAP9, AKIP1, AKIRIN1, AKIRIN2, AKR1A1, AKR7A2, AKT1, AKTIS1, AKTIP, ALAD, ALDH3A2, ALDH9A1, ALG11, ALG5, ALG8, ALG9, ALKBH1, ALKBH2, ALKBH3, ALKBH5, ALS2, ALYREF, AMBRA1, AMD1, ANAPC10, ANAPC11, ANAPC13, ANAPC15, ANAPC16, ANAPC2, ANAPC5, ANAPC7, ANKFY1, ANKH, ANKHD1, ANKHD1-EIF4EBP3, ANKRD10, ANKRD17, ANKRD28, ANKRD39, ANKRD46, ANO6, ANP32A, ANP32B, ANP32C, ANP32E, ANXA6, ANXA7, AP1B1, AP1G1, AP1M1, AP2A1, AP2A2, AP2M1, AP2S1, AP3B1, AP3D1, AP3M1, AP3S1, AP3S2, AP4B1, AP5M1, APEH, APEX1, APEX2, APH1A, API5, APIP, APOA1BP, APOL2, APOOL, APOPT1, APPL2, APTX, ARAF, ARCN1, ARF1, ARF5, ARF6, ARFGAP2, ARFGAP3, ARFGEF2, ARFIP1, ARFIP2, ARFRP1, ARHGAP35, ARHGAP5, ARHGDIA, ARHGEF10L, ARHGEF11, ARHGEF40, ARIH1, ARIH2, ARIH2OS, ARL1, ARL14EP, ARL5A, ARL6IP4, ARL8A, ARL8B, ARMC1, ARMC10, ARMC5, ARMC6, ARMC7, ARMC8, ARMCX3, ARMCX5, ARNT, ARPC1A, ARPC2, ARPC5L, ARV1, ASB1, ASB6, ASB7, ASB8, ASCC1, ASCC3, ASF1A, ASH2L, ASNA1, ASNSD1, ASPSCR1, ASUN, ASXL1, ATAD1, ATAD3A, ATE1, ATF1, ATF2, ATF4, ATF6, ATF7, ATF7IP, ATG12, ATG13, ATG16L1, ATG2A, ATG2B, ATG3, ATG4B, ATG4D, ATG5, ATG7, ATIC, ATL2, ATMIN, ATOX1, ATP2C1, ATP5A1, ATP5B, ATP5C1, ATP5D, ATP5F1, ATP5G2, ATP5G3, ATP5H, ATP5J, ATP5J2, ATP5J2-PTCD1, ATP5L, ATP5O, ATP5S, ATP5SL, ATP6AP1, ATP6V0A2, ATP6V0B, ATP6V0C, ATP6V0D1, ATP6V0E1, ATP6V1C1, ATP6V1D, ATP6V1E1, ATP6V1F, ATP6V1G1, ATP6V1H, ATPAF2, ATPIF1, ATRAID, ATRN, ATXN10, ATXN1L, ATXN2, ATXN2L, ATXN7L3, ATXN7L3B, AUH, AUP1, AURKAIP1, AXIN1, AZI2, AZIN1, B3GALT6, B4GALT3, B4GALT5, B4GALT7, BABAM1, BAD, BAG1, BAG4, BAG6, BAHD1, BANF1, BAP1, BAZ1B, BBS4, BCAP29, BCAP31, BCAS2, BCAT2, BCCIP, BCKDHA, BCKDK, BCL2L1, BCL2L13, BCL2L2-PABPN1, BCL7B, BCLAF1, BCS1L, BECN1, BFAR, BIRC2, BIVM-ERCC5, BLMH, BLOC1S1, BLOC1S2, BLOC1S3, BLOC1S4, BLOC1S6, BLZF1, BMI1, BMS1, BNIP1, BNIP2, BOD1, BOLA1, BOLA3, BPGM, BPNT1, BPTF, BRAT1, BRD2, BRD4, BRD7, BRD9, BRE, BRF1, BRF2, BRIX1, BRK1, BRMS1, BRPF1, BRPF3, BSDC1, BSG, BTBD2, BTD, BTF3, BUB3, BZW1, C10orf12, C10orf2, C10orf76, C10orf88, C11orf1, C11orf24, C11orf31, C11orf57, C11orf58, C11orf73, C11orf83, C12orf10, C12orf23, C12orf29, C12orf44, C12orf45, C12orf5, C12orf52, C12orf57, C12orf65, C12orf66, C14orf1, C14orf119, C14orf142, C14orf166, C14orf2, C14orf28, C15orf38-AP3S2, C15orf57, C16orf13, C16orf62, C16orf72, C16orf91, C17orf49, C17orf51, C17orf58, C17orf59, C17orf70, C17orf85, C18orf21, C18orf25, C18orf32, C18orf8, C19orf43, C19orf53, C19orf60, C19orf70, C1GALT1, C1QBP, C1orf109, C1orf122, C1orf123, C1orf174, C1orf43, C1orf50, C1orf52, C20orf111, C20orf24, C21orf2, C21orf33, C21orf59, C22orf28, C22orf29, C22orf32, C2orf47, C2orf49, C2orf69, C2orf74, C2orf76, C3orf17, C3orf37, C3orf38, C3orf58, C4orf27, C4orf3, C4orf52, C5orf15, C5orf24, C6orf1, C6orf106, C6orf120, C6orf136, C6orf226, C6orf47, C6orf57, C6orf62, C6orf89, C7orf25, C7orf26, C7orf49, C7orf50, C7orf55, C7orf55-LUC7L2, C7orf73, C8orf33, C8orf40, C8orf59, C8orf76, C8orf82, C9orf123, C9orf16, C9orf37, C9orf64, C9orf69, C9orf78, C9orf89, CAB39, CALCOCO2, CALM1, CALR, CALU, CAMTA1, CAMTA2, CANT1, CANX, CAPN1, CAPN7, CAPNS1, CAPRIN1, CAPZA2, CAPZB, CARKD, CARS, CARS2, CASC3, CASC4, CASP3, CASP7, CASP9, CBR4, CBX3, CBX5, CC2D1A, CC2D1B, CCAR1, CCBL1, CCDC12, CCDC124, CCDC127, CCDC130, CCDC137, CCDC149, CCDC174, CCDC22, CCDC23, CCDC25, CCDC47, CCDC50, CCDC51, CCDC59, CCDC71, CCDC86, CCDC90A, CCDC92, CCDC94, CCM2, CCNB1IP1, CCNDBP1, CCNG1, CCNH, CCNK, CCNL1, CCNL2, CCNY, CCPG1, CCT3, CCT4, CCT5, CCT6A, CCT7, CCT8, CD164, CD320, CD46, CD63, CD81, CD82, CD99L2, CDC123, CDC16, CDC23, CDC27, CDC37, CDC37L1, CDC40, CDC42, CDC5L, CDIP1, CDIPT, CDK12, CDK13, CDK16, CDK2AP1, CDK4, CDK5RAP1, CDK8, CDK9, CDS2, CDV3, CDYL, CEBPG, CEBPZ, CECR5, CELF1, CENPB, CENPT, CEP104, CEP57, CEP63, CERK, CERS2, CGGBP1, CHAMP1, CHCHD1, CHCHD2, CHCHD3, CHCHD4, CHCHD5, CHCHD7, CHD1L, CHD4, CHD8, CHERP, CHID1, CHKB, CHMP1A, CHMP2A, CHMP2B, CHMP4A, CHMP4B, CHMP5, CHMP6, CHP1, CHPT1, CHRAC1, CHST12, CHST7, CHTOP, CHUK, CHURC1, CHURC1-FNTB, CIAO1, CIB1, CIC, CINP, CIR1, CIRH1A, CISD1, CISD2, CISD3, CKAP4, CLCC1, CLCN3, CLCN7, CLINT1, CLK3, CLNS1A, CLOCK, CLP1, CLPP, CLPTM1, CLPTM1L, CLPX, CLTA, CLTB, CLTC, CMAS, CMC1, CMC2, CMC4, CMPK1, CNBP, CNIH, CNIH4, CNNM2, CNNM3, CNOT1, CNOT11, CNOT2, CNOT3, CNOT4, CNOT7, CNST, COA1, COA3, COA4, COA5, COA6, COASY, COG1, COG2, COG3, COG4, COG7, COG8, COMMD1, COMMD10, COMMD3, COMMD3-BMI1, COMMD5, COMMD6, COMMD7, COMMD9, COMT, COPA, COPB1, COPB2, COPE, COPG1, COPS2, COPS3, COPS4, COPS5, COPS6, COPS7A, COPS7B, COPS8, COPZ1, COQ10B, COQ2, COQ4, COQ5, COQ6, COROIC, COX11, COX14, COX15, COX16, COX19, COX20, COX4I1, COX5B, COX6B1, COX6C, COX7A2, COX7A2L, COX7C, COX8A, CPD, CPNE1, CPNE2, CPNE3, CPOX, CPSF2, CPSF3L, CPSF4, CPSF6, CPSF7, CRADD, CRBN, CRCP, CREB3, CREBZF, CREG1, CRELD1, CRIPAK, CRIPT, CRK, CRKL, CRLS1, CRNKL1, CRTC2, CRY2, CSGALNACT2, CSNK1A1, CSNK1A1L, CSNK1D, CSNKIG3, CSNK2A3, CSNK2B, CSRP2BP, CST3, CSTB, CSTF1, CSTF2T, CTAGE5, CTBP1, CTCF, CTDSP2, CTNNA1, CTNNB1, CTNNBIP1, CTNNBL1, CTNND1, CTSA, CTSD, CTTN, CTU2, CUEDC2, CUL1, CUL2, CUL4A, CUL4B, CUL5, CUTA, CUX1, CWC15, CWC22, CWC25, CXXC1, CXXC5, CXorf40A, CXorf40B, CXorf56, CYB5B, CYB5D2, CYB5R3, CYC1, CYFIP1, CYHR1, CYP2U1, D2HGDH, DAD1, DAG1, DAGLB, DALRD3, DAP3, DARS, DARS2, DAXX, DAZAP1, DBT, DCAF10, DCAF11, DCAF12, DCAF13, DCAF5, DCAF7, DCAF8, DCAKD, DCTD, DCTN2, DCTN3, DCTN4, DCTN5, DCTN6, DCTPP1, DCUN1D3, DCUN1D4, DCUN1D5, DDA1, DDB1, DDB2, DDOST, DDRGK1, DDX1, DDX10, DDX17, DDX18, DDX19A, DDX19B, DDX21, DDX23, DDX24, DDX27, DDX39B, DDX3X, DDX41, DDX42, DDX46, DDX47, DDX49, DDX54, DDX56, DDX59, DEDD, DEF8, DEGS1, DEK, DENND1A, DENND4A, DENR, DERA, DERL1, DERL2, DESI1, DEX1, DFFA, DGCR14, DGCR2, DGCR6L, DHPS, DHRS12, DHRS7B, DHX15, DHX16, DHX29, DHX30, DHX32, DHX33, DHX36, DHX38, DHX8, DHX9, DIABLO, DIDO1, DIEXF, DIMT1, DIRC2, DIS3, DIS3L2, DKC1, DLD, DLG1, DLGAP4, DLST, DMAP1, DNAAF2, DNAJA2, DNAJA3, DNAJB11, DNAJB12, DNAJB9, DNAJC10, DNAJC11, DNAJC14, DNAJC17, DNAJC19, DNAJC2, DNAJC21, DNAJC3, DNAJC4, DNAJC5, DNAJC7, DNAJC8, DNAJC9, DNASE2, DNLZ, DNM1L, DNM2, DNTTIP1, DNTTIP2, DOHH, DOLK, DPAGT1, DPH1, DPH2, DPH3, DPH5, DPM1, DPP7, DPY30, DR1, DRAM2, DRAP1, DRG2, DROSHA, DSCR3, DTWD1, DUSP11, DUSP14, DUSP16, DUSP22, DUT, DVL3, DYM, DYNCILI1, DYNLL2, DYNLRB1, DYNLT1, E2F4, E4F1, EAF1, EAPP, EARS2, EBAG9, EBNAIBP2, ECD, ECH1, ECHDC1, ECHS1, ECI1, ECI2, ECSIT, EDC3, EDC4, EDEM3, EDF1, EED, EEF1B2, EEF1E1, EEF2, EEFSEC, EFCAB14, EFHA1, EFR3A, EFTUD1, EFTUD2, EGLN2, EHMT1, E124, EID2, EIF1, EIF1AD, EIF1B, EIF2A, EIF2AK1, EIF2AK3, EIF2AK4, EIF2B2, EIF2B3, EIF2B4, EIF2B5, EIF2D, EIF2S1, EIF2S2, EIF3A, EIF3B, EIF3D, EIF3E, EIF3G, EIF3H, EIF31, EIF3J, EIF3K, EIF3L, EIF3M, EIF4A1, EIF4A3, EIF4E2, EIF4G1, EIF4G2, EIF4G3, EIF4H, EIF5, EIF5A1, EIF5B, EIF6, ELAC2, ELAVL1, ELF2, ELK1, ELK4, ELL2, ELMOD3, ELOVL1, ELP2, ELP3, ELP4, ELP6, EMC1, EMC10, EMC2, EMC3, EMC4, EMC6, EMC7, EMC8, EMC9, EMD, EMG1, ENDOG, ENOPH1, ENSA, ENTPD4, ENTPD6, ENY2, EPC1, EPM2AIP1, EPN1, EPRS, ERAL1, ERAP1, ERCC1, ERCC2, ERCC3, ERCC5, ERGIC2, ERGIC3, ERH, ERI3, ERICH1, ERLEC1, ERO1L, ERP44, ESD, ESF1, ETF1, ETFA, ETFB, ETV6, EWSR1, EXD2, EXOC1, EXOC2, EXOC3, EXOC4, EXOC7, EXOC8, EXOSC1, EXOSC10, EXOSC2, EXOSC4, EXOSC7, EXOSC8, EXT2, EXTL3, FADD, FAF1, FAF2, FAHD1, FAM104B, FAMI08A1, FAM108B1, FAM114A2, FAM118B, FAM120A, FAM120AOS, FAM120B, FAM122A, FAM127B, FAM134A, FAM134C, FAM136A, FAM149B1, FAM160A2, FAM160B1, FAM160B2, FAM162A, FAM168B, FAM173A, FAM173B, FAM174A, FAM175B, FAM177A1, FAM178A, FAM192A, FAM199X, FAM200A, FAM204A, FAM206A, FAM208B, FAM20B, FAM210B, FAM232A, FAM35A, FAM3A, FAM50A, FAM50B, FAM58A, FAM63A, FAM73B, FAM8A1, FAM96A, FAM96B, FAM98A, FARS2, FARSA, FARSB, FASTK, FASTKD2, FASTKD5, FBRSL1, FBXL15, FBXL17, FBXL3, FBXL4, FBXL5, FBXL6, FBXO11, FBXO18, FBXO22, FBXO28, FBXO3, FBXO38, FBXO42, FBXO45, FBXO6, FBXO7, FBXW11, FBXW2, FBXW4, FBXW5, FBXW7, FCF1, FDFT1, FDPS, FDX1, FECH, FEM1C, FEN1, FEZ2, FGFR 1OP2, FH, FIBP, FICD, FIPIL1, FIS1, FIZ1, FKBP3, FKBP8, FKBPL, FKRP, FLAD1, FLCN, FLOT1, FLOT2, FNDC3A, FNTA, FNTB, FOPNL, FOXK2, FOXP4, FOXRED1, FPGS, FPGT, FRA1OAC1, FTO, FTSJ1, FTSJ2, FTSJ3, FTSJD1, FTSJD2, FUBP1, FUK, FUNDC2, FXN, FYTTD1, FZR1, G3BP1, GAA, GABARAP, GABARAPL2, GABPB1, GAPDH, GADD45GIP1, GALK2, GALNS, GALNT1, GALNT2, GALT, GANAB, GAPVD1, GARS, GART, GATAD2A, GATAD2B, GATC, GBA, GBA2, GBF1, GCC1, GCDH, GCLC, GCLM, GDE1, GDI2, GDPGP1, GGCT, GGNBP2, GGT7, GHDC, GHI™, GID8, GINM1, GIPC1, GLCE, GLE1, GLG1, GLI4, GLO1, GLRX2, GLRX3, GLRX5, GLT8D1, GLTP, GLTPD1, GLYR1, GMPPA, GMPR2, GNB1, GNB2, GNE, GNL2, GNL3, GNPAT, GNPDA1, GNPNAT1, GNPTG, GNS, GOLGA1, GOLGA2, GOLGA3, GOLGA5, GOLGA7, GOLGB1, GOLPH3, GOLTIB, GOPC, GORASP1, GORASP2, GOSR1, GOSR2, GPAA1, GPANK1, GPATCH4, GPBP1, GPBP1L1, GPHN, GP1, GPKOW, GPN1, GPN2, GPN3, GPR107, GPR108, GPS1, GPS2, GPX4, GRAMD4, GRHPR, GRINA, GRIPAP1, GRPEL1, GRSF1, GRWD1, GSK3A, GSK3B, GSPT1, GSPT2, GSR, GSS, GSTK1, GSTM4, GSTO1, GTDC2, GTF2A1, GTF2B, GTF2F1, GTF2F2, GTF2H1, GTF2H4, GTF2H5, GTF21, GTF3A, GTF3C1, GTF3C2, GTF3C3, GTF3C5, GTF3C6, GTPBP10, GTPBP4, GTPBP5, GTPBP8, GUK1, GUSB, GZF1, H1FX, H2AFV, H2AFX, H2AFY, H2AFZ, HADH, HADHA, HAGH, HARS, HARS2, HAT1, HAUS3, HAUS4, HAUS7, HAX1, HBP1, HBS1L, HCCS, HCFC1, HDAC2, HDAC3, HDAC6, HDAC8, HDDC3, HDGF, HDHD3, HDLBP, HEATR2, HEATRSA, HEBP1, HECTD3, HELZ, HEMK1, HERC4, HERPUD1, HERPUD2, HEXA, HEXDC, HEXIM1, HGS, HIAT1, HIATL1, HIBADH, HIGDIA, HIGD2A, HINFP, HINT1, HINT2, HISTIH2BC, HIVEP1, HMBS, HMG20A, HMG20B, HMGB1, HMGN3, HMGXB3, HMGXB4, HMOX2, HNIL, HNRNPAO, HNRNPA2B1, HNRNPAB, HNRNPC, HNRNPD, HNRNPF, HNRNPH1, HNRNPH2, HNRNPK, HNRNPL, HNRNPM, HNRNPR, HNRNPU, HNRNPUL1, HNRNPUL2, HNRPDL, HNRPLL, HPRT1, HP1BP3, HPS1, HPS6, HS1BP3, HS2ST1, HS6ST1, HSBP1, HSCB, HSD17B10, HSD17B12, HSD17B4, HSPA14, HSPA4, HSPA5, HSPA8, HSPA9, HSPBP1, HSPE1-MOB4, HTATIP2, HTRA2, HTT, HUS1, HUWE1, HYOU1, HYPK, IAH1, IARS, IARS2, IBA57, IBTK, ICK, ICMT, ICT1, IDE, IDH3A, IDH3B, IDH3G, IDI1, IER3IP1, IFNAR1, IFNGR1, IFRD1, IFT27, IKZF5, IL13RA1, IL6ST, ILF2, ILKAP, ILVBL, IMMT, IMP3, IMP4, IMPAD1, INF2, ING1, INO80B, INO80E, INPP5A, INPP5K, INSIG2, INTS1, INTS10, INTS12, INTS3, INTS4, INVS, IP6K1, IP6K2, IP07, IP08, IP09, IRAK1, IREB2, IRF2BP1, IRF2BP2, IRF2BPL, IRGQ, ISCU, ISOC2, IST1, ISY1, ISY1-RAB43, ITCH, ITFG1, ITFG3, ITGB1, ITGB1BP1, ITM2B, ITPA, ITPK1, ITPKC, ITPRIPL2, IVNS1ABP, IWS1, JAGN1, JAK1, JKAMP, JMJD4, JMJD6, JMJD7, JMJD8, JOSD2, JTB, JUND, KANSL2, KANSL3, KARS, KAT2B, KAT5, KAT8, KBTBD2, KBTBD4, KBTBD7, KCMF1, KCTD20, KCTD21, KCTD6, KDM2A, KDM4A, KDM5C, KDSR, KHDRBS1, KHNYN, KHSRP, KIAA0100, KIAA0141, KIAA0195, KIAA0196, KIAA0232, KIAA0319L, KIAA0391, KIAA0754, KIAA0947, KIAA1143, KIAA1191, KIAA1429, KIAA1430, KIAA1586, KIAA1704, KIAA1715, KIAA1919, KIAA1967, KIAA2013, KLC4, KLF3, KLF9, KLHDC2, KLHDC3, KLHL20, KLHL25, KLHL36, KLHL5, KLHL8, KPNA1, KPNB1, KRCC1, KRR1, KTI12, KTN1, KXD1, L3MBTL2, LACTB, LAGE3, LAMP1, LAMP2, LAMTOR1, LAMTOR2, LAMTOR3, LAMTOR4, LAMTOR5, LAP3, LAPTM4A, LARP1, LARP4, LARP7, LARS2, LCOR, LDHA, LEMD2, LENG1, LEPROT, LETM1, LETMD1, LGALSL, LHPP, LIAS, LIG3, LIG4, LIN37, LIN54, LIN7C, LINS, LIPT1, LMAN1, LMBRD1, LMF2, LMO4, LNX2, LOC100129361, LOC100289561, LOC441155, LOC729020, LONP1, LONP2, LPCAT3, LPIN1, LPPR2, LRFN3, LRPAP1, LRPPRC, LRRC14, LRRC24, LRRC28, LRRC40, LRRC41, LRRC42, LRRC47, LRRC57, LRRC59, LRRC8A, LRRFIP2, LRSAM1, LSG1, LSM1, LSM10, LSM14A, LSM14B, LSM2, LSM3, LSM4, LSM5, LSM6, LSM7, LSMD1, LSS, LTV1, LUC7L2, LUC7L3, LUZP6, LYRM1, LYRM4, LYRM5, LYSMD1, LYSMD3, LYSMD4, LZTR1, M6PR, MAD2L1BP, MAD2L2, MAEA, MAGED1, MAGEF1, MAGOH, MAGT1, MAK16, MALSU1, MAN1A2, MAN1B1, MAN2A2, MAN2B2, MAN2C1, MAP1LC3B2, MAP2K1, MAP2K2, MAP2K5, MAP3K7, MAP4K4, MAPK1, MAPK1IP1L, MAPK6, MAPK8, MAPK9, MAPKAP1, MAPKAPK2, MAPKAPK5, MAPRE2, MARCH2, MARCH5, MARCH6, MARCH7, MARK3, MARK4, MARS, MARS2, MAT2B, MAVS, MAX, MAZ, MBD1, MBD2, MBD3, MBD4, MBLAC1, MBNL2, MBTPS1, MBTPS2, MCAT, MCCC1, MCEE, MCFD2, MCM3AP, MCM7, MCMBP, MCOLN1, MCPH1, MCRS1, MCTS1, MCU, MDC1, MDP1, ME2, MEAF6, MECP2, MED10, MED11, MED13, MED14, MED16, MED19, MED20, MED21, MED24, MED29, MED31, MED4, MED6, MED7, MED8, MEF2A, MEF2BNB, MEMO1, MEN1, MEPCE, METAP1, METAP2, METRN, METTL13, METTL14, METTL16, METTL17, METTL18, METTL20, METTL21A, METTL23, METTL2A, METTL2B, METTL3, METTL5, MFAP1, MFAP3, MFF, MFN1, MFSD11, MFSD12, MFSD3, MFSD5, MGAT2, MGAT4B, MGME1, MGMT, MGRN1, MGST3, MIA3, MIB1, MICALL1, MICU1, MID1IP1, MIDN, MIEN1, MIER1, MIF, MIF4GD, MIIP, MINOS1, MIS12, MITD1, MKI67IP, MKKS, MKLN1, MKNK1, MKRN2, MLEC, MLF2, MLH1, MLLT1, MLLT10, MLST8, MLX, MMAA, MMADHC, MMS19, MNAT1, MNF1, MOB4, MOGS, MON1A, MON2, MORC2, MORF4L2, MOSPD1, MPC2, MPDU1, MPG, MPHOSPH10, MP1, MPLKIP, MPND, MPPE1, MPV17L2, MRFAP1, MRFAPIL1, MRI1, MRM1, MRP63, MRPL1, MRPL10, MRPL11, MRPL12, MRPL13, MRPL14, MRPL15, MRPL16, MRPL17, MRPL18, MRPL19, MRPL2, MRPL20, MRPL21, MRPL22, MRPL23, MRPL24, MRPL27, MRPL28, MRPL3, MRPL30, MRPL32, MRPL33, MRPL35, MRPL36, MRPL37, MRPL38, MRPL4, MRPL40, MRPL41, MRPL42, MRPL43, MRPL44, MRPL45, MRPL46, MRPL47, MRPL48, MRPL49, MRPL50, MRPL51, MRPL52, MRPL53, MRPL54, MRPL55, MRPL9, MRPS10, MRPS11, MRPS12, MRPS14, MRPS15, MRPS16, MRPS17, MRPS18A, MRPS18B, MRPS18C, MRPS2, MRPS21, MRPS22, MRPS23, MRPS24, MRPS25, MRPS26, MRPS27, MRPS28, MRPS30, MRPS31, MRPS33, MRPS34, MRPS35, MRPS5, MRPS6, MRPS7, MRPS9, MRRF, MRS2, MRTO4, MSANTD3, MSH3, MSH6, MSL3, MSMP, MSRA, MSRB2, MTA2, MTCH1, MTCH2, MTDH, MTERFD1, MTERFD2, MTERFD3, MTFMT, MTFR1, MTFR1L, MTIF3, MTM1, MTMR1, MTMR3, MTMR6, MTO1, MTPAP, MTRR, MTSS1, MTX2, MUL1, MUS81, MUT, MVD, MXD4, MXI1, MYBBP1A, MYEOV2, MYL12B, MYNN, MYO1E, MYPOP, MZF1, MZT2A, MZT2B, N4BP1, N4BP2L2, NAA10, NAA15, NAA20, NAA38, NAA50, NAA60, NABP2, NACA, NACA2, NACC1, NACC2, NAE1, NAMPT, NANS, NAP1L4, NAPA, NARF, NARFL, NARG2, NARS, NARS2, NAT10, NBN, NBR1, NCAPH2, NCBP2, NCK1, NCKIPSD, NCL, NCLN, NCOA1, NCOA6, NCOR1, NCSTN, NDEL1, NDFIP1, NDNL2, NDST1, NDUFA10, NDUFA11, NDUFA12, NDUFA13, NDUFA2, NDUFA3, NDUFA4, NDUFA5, NDUFA6, NDUFA7, NDUFA8, NDUFA9, NDUFAF2, NDUFAF3, NDUFAF4, NDUFB10, NDUFB11, NDUFB2, NDUFB3, NDUFB4, NDUFB5, NDUFB6, NDUFB7, NDUFB8, NDUFB9, NDUFC1, NDUFC2, NDUFC2-KCTD14, NDUFS2, NDUFS3, NDUFS4, NDUFS5, NDUFS6, NDUFS7, NDUFS8, NDUFV1, NDUFV2, NECAP1, NEDD8, NEDD8-MDP1, NEIL2, NEK4, NEK9, NELFB, NELFCD, NELFE, NENF, NEU1, NF2, NFATC2IP, NFE2L2, NFIL3, NFKBIB, NFKBIL1, NFU1, NFX1, NFYB, NFYC, NGDN, NGLY1, NGRN, NHP2, NHP2L1, NIF3L1, NINJ1, NIP7, NIPA2, NIPBL, NISCH, NIT1, NIT2, NKAP, NKIRAS2, NMD3, NME1-NME2, NME2, NME3, NME6, NMRK1, NMT1, NOA1, NOB1, NOC2L, NOL10, NOL11, NOL12, NOL6, NOL7, NOL8, NOLC1, NOM1, NONO, NOP10, NOP14, NOP16, NOP2, NOP56, NOP58, NOP9, NPC1, NPC2, NPLOC4, NPRL2, NPRL3, NQO2, NR1H2, NR2C1, NR2C2AP, NR3C2, NRBP1, NRDE2, NRIP1, NSA2, NSD1, NSDHL, NSFL1C, NSMCE1, NSMCE2, NSMCE4A, NSRP1, NSUN2, NSUN5, NSUN6, NT5C, NT5C3, NT5DC1, NTAN1, NTMT1, NTPCR, NUB1, NUBP1, NUBP2, NUCB1, NUCKS1, NUDC, NUDCD1, NUDCD2, NUDT14, NUDT15, NUDT2, NUDT21, NUDT22, NUDT3, NUDT9, NUFIP2, NUP107, NUP133, NUP153, NUP54, NUP62, NUP85, NUPL2, NUTF2, NXF1, NXT1, OAT, OAZ1, OAZ2, OBFC1, OCEL1, OCIAD1, ODC1, OGFOD1, OGFOD3, OGFR, OGG1, OGT, OLA1, OPA1, OPA3, ORC4, ORMDL1, ORMDL2, ORMDL3, OS9, OSBP, OSBPL2, OSBPL9, OSGEP, OSGIN2, OSTM1, OTUB1, OTUD5, OVCA2, OXA1L, OXNAD1, P4HTM, PA2G4, PABPN1, PACSIN2, PAF, PAFAHIB1, PAGR1, PAICS, PAIP1, PAIP2, PAK1IP1, PAK2, PAM16, PANK2, PANK3, PANK4, PANX1, PAPD4, PAPD7, PAPOLA, PARK7, PARL, PARN, PARP1, PARP3, PARP9, PATL1, PATZ1, PAXBP1, PBDC1, PBX2, PCBP1, PCBP2, PCDHGB5, PCF11, PCGF1, PCGF5, PCID2, PCIF1, PCM1, PCMT1, PCNA, PCNX, PCNXL4, PCSK7, PCYOX1, PCYTIA, PDAP1, PDCD2, PDCD5, PDCD6, PDCD6IP, PDE12, PDE6D, PDGFC, PDHB, PDHX, PDK2, PDLIM5, PDP2, PDS5A, PDZD11, PDZD8, PEBP1, PEF1, PELO, PELP1, PEPD, PES1, PET100, PET117, PEX1, PEX11A, PEX11B, PEX12, PEX13, PEX14, PEX16, PEX19, PEX2, PEX26, PEX5, PEX6, PFDN2, PFDN4, PFDN5, PFDN6, PFN1, PGAM5, PGBD3, PGK1, PGLS, PGP, PGPEP1, PGRMC2, PHACTR4, PHAX, PHB, PHB2, PHC2, PHF10, PHF12, PHF20L1, PHF23, PHF5A, PHKB, PHPT1, PHRF1, PI4K2A, PI4KA, P14 KB, PIAS1, PICALM, PICK1, PIGC, PIGF, PIGG, PIGH, PIGK, PIGP, PIGS, PIGT, PIGU, PIGW, PIGX, PIGY, PIH1D1, PIK3C3, PIK3CB, PIK3R1, PIK3R4, PIN1, PINK1, PINX1, PIP5K1A, PITHD1, PITPNA, PITPNB, PITRM1, PLA2G12A, PLAA, PLBD2, PLD3, PLEKHA1, PLEKHJ1, PLEKHM1, PLGRKT, PLIN3, PLOD1, PLOD3, PLRG1, PMF1, PMF1-BGLAP, PMPCA, PMPCB, PMS1, PMVK, PNISR, PNKD, PNKP, PNN, PNO1; PNPLA6, PNPLA8, PNPO, PNPT1, PNRC2, POFUT1, POLD2, POLDIP2, POLDIP3, POLE3, POLE4, POLG, POLH, POLK, POLL, POLM, POLR1C, POLR1D, POLR1E, POLR2A, POLR2B, POLR2C, POLR2D, POLR2E, POLR2F, POLR2G, POLR2H, POLR21, POLR2J, POLR2K, POLR2L, POLR3C, POLR3E, POLR3GL, POLR3K, POM121, POM121C, POMGNT1, POMP, POMT1, POP4, POP5, POP7, PPA1, PPA2, PPAN, PPAN-P2RY11, PPARA, PPARD, PPCS, PPFIA1, PPHLN1, PPID, PPIE, PPIF, PPIG, PPIH, PPIL4, PPM1A, PPM1B, PPPICA, PPPICC, PPP1R10, PPP1R11, PPP1R15B, PPP1 R37, PPP1R7, PPP1 R8, PPP2CA, PPP2CB, PPP2R1A, PPP2R2A, PPP2R2D, PPP2R3C, PPP2R4, PPP2R5A, PPP2R5B, PPP2R5C, PPP2R5D, PPP2R5E, PPP4C, PPP4R1, PPP4R2, PPP5C, PPP6C, PPP6R2, PPP6R3, PPWD1, PQBP1, PQLC1, PQLC2, PRADC1, PRCC, PRDM4, PRDX1, PRDX2, PRDX3, PRDX5, PRDX6, PREB, PREP, PRKAA1, PRKAB1, PRKACA, PRKAG1, PRKARIA, PRKRIP1, PRMT1, PRMT5, PRMT7, PROSC, PRPF18, PRPF19, PRPF3, PRPF31, PRPF4, PRPF40A, PRPF4B, PRPF6, PRPF8, PRPS1, PRPSAP1, PRR14, PRRC1, PRRC2A, PRRC2B, PRUNE, PSEN1, PSEN2, PSENEN, PSKH1, PSMA1, PSMA2, PSMA3, PSMA4, PSMA5, PSMA6, PSMA7, PSMB1, PSMB2, PSMB3, PSMB4, PSMB5, PSMB6, PSMB7, PSMC2, PSMC3, PSMC4, PSMC5, PSMC6, PSMD1, PSMD10, PSMD11, PSMD12, PSMD13, PSMD14, PSMD2, PSMD3, PSMD4, PSMD5, PSMD6, PSMD7, PSMD8, PSMD9, PSME1, PSME3, PSMF1, PSMG2, PSMG3, PSMG4, PSPC1, PTCD1, PTCD3, PTDSS1, PTEN, PTGES2, PTGES3, PTOV1, PTP4A2, PTPMT1, PTPN1, PTPNI1, PTPN23, PTRH1, PTRH2, PTRHD1, PUF60, PUM1, PUM2, *PURA*, PURB, PUS3, PUS7, PUSL1, PWP1, PWP2, PWWP2A, PXMP4, PYCR2, PYGO2, PYURF, QARS, QRICH1, QRSL1, QSOX1, QTRT1, R3HCC1, R3HDM2, RAB10, RAB11A, RAB11B, RAB14, RAB18, RAB1A, RAB1B, RAB21, RAB22A, RAB2A, RAB2B, RAB3GAP1, RAB3GAP2, RAB40C, RAB4A, RAB5A, RAB5B, RAB5C, RAB6A, RAB7A, RAB9A, RABEP1, RABEPK, RABGEF1, RABGGTA, RABGGTB, RAD1, RAD17, RAD23B, RAD50, RAD51C, RAF1, RALA, RALBP1, RALY, RAN, RANBP1, RANBP2, RANBP3, RANBP6, RANGAP1, RANGRF, RAP1A, RAPGEF1, RAPGEF2, RARS, RARS2, RB1CC1, RBAK, RBBP4, RBBP7, RBCK1, RBFA, RBM10, RBM12, RBM12B, RBM14, RBM14-RBM4, RBM15, RBM15B, RBM17, RBM18, RBM19, RBM23, RBM27, RBM28, RBM33, RBM34, RBM39, RBM4, RBM41, RBM42, RBM5, RBM6, RBM7, RBM8A, RBMX, RBMXL1, RBX1, RC3H2, RCAN1, RCHY1, RCN2, RDH14, RDX, REEP3, REEP5, RELA, REPIN1, REPS1, RER1, REST, REXO1, RFC1, RFC2, RFC5, RFK, RFNG, RFT1, RFWD2, RFXANK, RGP1, RHBDD1, RHBDD3, RHOA, RHOB, RHOT1, RHOT2, RIC8A, RIN2, RING1, RINT1, RIOK1, RIOK2, RIOK3, RIPK1, RMDN1, RMDN3, RMI1, RMND1, RMND5A, RMND5B, RNASEH1, RNASEH2C, RNASEK, RNF10, RNF103, RNF11, RNF111, RNF113A, RNF115, RNF121, RNF126, RNF13, RNF14, RNF141, RNF146, RNF167, RNF181, RNF185, RNF187, RNF216, RNF220, RNF25, RNF26, RNF31, RNF34, RNF4, RNF40, RNF5, RNF6, RNF7, RNH1, RNMTL1, RNPEP, ROMO1, RP9, RPA2, RPA3, RPAIN, RPAP3, RPF1, RPF2, RPL10A, RPL11, RPL14, RPL26L1, RPL27, RPL30, RPL31, RPL32, RPL34, RPL35, RPL35A, RPL36AL, RPL4, RPL6, RPL7L1, RPL8, RPN1, RPN2, RPP14, RPP25L, RPP30, RPP38, RPRDIB, RPS13, RPS19BP1, RPS23, RPS24, RPS27L, RPS5, RPS6, RPS6KA3, RPS6KB1, RPS6KB2, RPUSD3, RQCD1, RRAGA, RRM1, RRN3, RRNAD1, RRP1, RRP36, RRP7A, RRP8, RRS1, RSAD1, RSBN1L, RSC1A1, RSL1D1, RSPRY1, RSRC1, RSRC2, RTCA, RTFDC1, RTN4, RUFY1, RUVBL1, RWDD1, RWDD3, RXRA, RXRB, SAE1, SAMD1, SAMD4B, SAMD8, SAMM50, SAP18, SAP30, SAP30BP, SAP30L, SAR1A, SARNP, SARS, SART1, SART3, SAT2, SAV1, SBDS, SCAF1, SCAF11, SCAF4, SCAF8, SCAMP2, SCAMP3, SCAND1, SCAP, SCARB2, SCFD1, SCFD2, SCNM1, SCO1, SCO2, SCOC, SCP2, SCRIB, SCRN3, SCYL1, SCYL2, SCYL3, SDAD1, SDCBP, SDCCAG3, SDCCAG8, SDE2, SDF2, SDF4, SDHA, SDHAF2, SDHB, SDHC, SDHD, SDR39U1, SEC11A, SEC13, SEC16A, SEC22B, SEC22C, SEC23A, SEC23IP, SEC24A, SEC24B, SEC24C, SEC31A, SEC61A1, SEC61B, SEC61G, SEC62, SEC63, SECISBP2, SEH1L, SEL1L, SELK, SELO, SELRC1, SELT, SENP2, SENP3, SENP5, SENP6, SEPHS1, SERBP1, SERF2, SERGEF, SERINC1, SERINC3, SERPINB6, SERTAD2, SET, SETD2, SETD3, SETD5, SETD6, SETD7, SETD8, SETDB1, SF1, SF3A1, SF3A3, SF3B1, SF3B14, SF3B2, SF3B3, SF3B4, SF3B5, SFSWAP, SGK196, SGMS1, SGPL1, SGSM3, SGTA, SH3BP5L, SH3GLB1, SHARPIN, SHOC2, SIAH1, SIAH2, SIGMAR1, SIKE1, SIL1, SIRT2, SIRT3, SIRT5, SIRT6, SIVA1, SKIL, SKIV2L, SKIV2L2, SKP1, SLC15A4, SLC20A1, SLC25A11, SLC25A26, SLC25A28, SLC25A3, SLC25A32, SLC25A38, SLC25A39, SLC25A44, SLC25A46, SLC25A5, SLC27A4, SLC30A1, SLC30A5, SLC30A9, SLC35A2, SLC35A4, SLC35B1, SLC35B2, SLC35C2, SLC35E1, SLC35E3, SLC35F5, SLC38A2, SLC39A1, SLC39A3, SLC39A7, SLC41A3, SLC46A3, SLC48A1, SLIRP, SLMO2, SL™, SMAD2, SMAD4, SMAD5, SMAP1, SMARCA2, SMARCA4, SMARCAL1, SMARCB1, SMARCE1, SMC1A, SMC5, SMCR7L, SMEK1, SMEK2, SMG5, SMG7, SMG8, SMIM11, SMIM12, SMIM8, SMNDC1, SMPD1, SMPD4, SMU1, SMUG1, SNAP23, SNAP29, SNAP47, SNAPC3, SNAPC5, SNAPIN, SND1, SNF8, SNRNP200, SNRNP25, SNRNP27, SNRNP35, SNRNP40, SNRNP48, SNRNP70, SNRPA, SNRPB, SNRPB2, SNRPC, SNRPD1, SNRPD2, SNRPD3, SNRPG, SNUPN, SNW1, SNX12, SNX13, SNX17, SNX18, SNX19, SNX2, SNX25, SNX3, SNX4, SNX5, SNX6, SNX9, SOCS4, SOCS6, SOD1, SON, SPAG7, SPAG9, SPATA2, SPATASL1, SPCS1, SPCS3, SPECCIL, SPEN, SPG11, SPG21, SPG7, SPHAR, SPNS1, SPOP, SPPL2B, SPPL3, SPRYD3, SPRYD7, SPSB3, SPTSSA, SPTY2D1, SRA1, SRD5A3, SREBF2, SREK1IP1, SRM, SRP14, SRP19, SRP54, SRP68, SRP72, SRP9, SRPR, SRPRB, SRR, SRRD, SRRM1, SRSF1, SRSF10, SRSFI1, SRSF2, SRSF3, SRSF4, SRSF7, SRSF8, SS18L2, SSB, SSBP1, SSNA1, SSR1, SSR2, SSR3, SSRP1, SSSCA1, SSU72, ST3GAL2, ST6GALNAC6, ST7, STAM, STAM2, STAMBP, STARD3, STARD7, STAT3, STAU1, STAU2, STIM1, STIP1, STK11, STK16, STOM, STOML1, STOML2, STRAP, STRIP1, STRN3, STT3A, STT3B, STUB1, STX10, STX17, STX4, STX5, STX8, STXBP3, STYXL1, SUB1, SUCLA2, SUCLG1, SUCLG2, SUGP1, SUGT1, SUMO1, SUMO3, SUN2, SUPT4H1, SUPT5H, SUPT6H, SUPT7L, SUPV3L1, SURF1, SURF4, SURF6, SUV420H1, SUZ12, SYAP1, SYF2, SYMPK, SYNCRIP, SYNJ2BP, SYNJ2BP-COX16, SYPL1, SYS1, SYVN1, SZRD1, TAB1, TAB2, TACO1, TADA1, TADA3, TAF10, TAF11, TAF12, TAF13, TAF15, TAF1D, TAF4, TAF5L, TAF8, TAF9, TALDO1, TAMM41, TANGO2, TANGO6, TANK, TAOK2, TAPBP, TAPT1, TARDBP, TARS, TATDN1, TATDN2, TAX1BP1, TAZ, TBC1D1, TBC1D14, TBC1D15, TBC1D20, TBC1D22A, TBC1D23, TBC1D7, TBC1D9B, TBCA, TBCB, TBCC, TBCCD1, TBCD, TBCE, TBK1, TBP, TBRG1, TBRG4, TCAIM, TCEANC2, TCEB1, TCEB2, TCEB3, TCERG1, TCF12, TCF20, TCF25, TCP1, TCTN3, TDP2, TDRD3, TECR, TEF, TEFM, TELO2, TERF2, TERF2IP, TEX2, TEX261, TEX264, TFAM, TFB1M, TFB2M, TFCP2, TFDP1, TFE3, TFG, TFIP11, TFPT, TGIF2-C20orf24, TGOLN2, THADA, THAP3, THAP4, THAP5, THAP7, THOC5, THOC7, THOP1, THRAP3, THTPA, THUMPD3, THYN1, TIA1, TIAL1, TICAM1, TIGD5, TIGD6, TIMM10, TIMM10B, TIMM13, TIMM17A, TIMM17B, TIMM21, TIMM22, TIMM44, TIMM50, TIMM8B, TIMM9, TIMMDC1, TINF2, TIPRL, TJAP1, TLE1, TLK1, TM2D1, TM2D2, TM2D3, TM9SF1, TM9SF2, TM9SF3, TM9SF4, TMBIM1, TMBIM4, TMBIM6, TMCC1, TMCO1, TMCO3, TMED1, TMED10, TMED2, TMED4, TMED5, TMED7, TMED7-TICAM2, TMED9, TMEM101, TMEM106B, TMEM106C, TMEM115, TMEM120A, TMEM126A, TMEM127, TMEM128, TMEM129, TMEM131, TMEM134, TMEM141, TMEM147, TMEM14B, TMEM14C, TMEM161A, TMEM167B, TMEM168, TMEM177, TMEM179B, TMEM18, TMEM184C, TMEM185B, TMEM186, TMEM187, TMEM189, TMEM189-UBE2V1, TMEM19, TMEM192, TMEM199, TMEM203, TMEM205, TMEM214, TMEM219, TMEM222, TMEM223, TMEM230, TMEM242, TMEM248, TMEM251, TMEM256, TMEM258, TMEM259, TMEM30A, TMEM33, TMEM39A, TMEM41A, TMEM41B, TMEM42, TMEM5, TMEM50A, TMEM50B, TMEM55B, TMEM57, TMEM59, TMEM60, TMEM62, TMEM63B, TMEM64, TMEM66, TMEM69, TMEM70, TMEM81, TMEM87A, TMEM9, TMEM9B, TMF1, TMLHE, TMPO, TMUB1, TMUB2, TMX1, TMX2, TMX4, TNFAIP1, TNFAIP8L2-SCNM1, TNIP1, TNKS2, TNPO1, TNPO3, TNRC6A, TOB1, TOLLIP, TOMM20, TOMM22, TOMM40, TOMM5, TOMM6, TOMM7, TOMM70A, TOP1, TOP2B, TOPORS, TOR1A, TOR1AIP2, TOR1B, TOR3A, TOX4, TP53RK, TPCN1, TPD52L2, TPGS1, TPI1, TPP2, TPRA1, TPRGIL, TPRKB, TPRN, TPST2, TRA2A, TRA2B, TRAF6, TRAF7, TRAP1, TRAPPC1, TRAPPC10, TRAPPC11, TRAPPC12, TRAPPC13, TRAPPC2L, TRAPPC3, TRAPPC4, TRAPPC5, TRAPPC6B, TRAPPC8, TRAPPC9, TRIAP1, TRIM26, TRIM27, TRIM28, TRIM3, TRIM39, TRIM39-RPP21, TRIM41, TRIM44, TRIM56, TRIM65, TRIM8, TRIP12, TRIP4, TRMT1, TRMT10C, TRMT112, TRMT12, TRMT1L, TRMT2A, TRNAU1AP, TRNT1, TRPC4AP, TRPT1, TRUB2, TSC2, TSEN15, TSEN34, TSFM, TSG101, TSN, TSNAX, TSPAN17, TSPAN31, TSPYL1, TSR1, TSR2, TSR3, TSSC4, TSTA3, TSTD2, TTC1, TTC17, TTC19, TTC32, TTC33, TTC37, TTC4, TTC7B, TTC9C, TTI1, TTI2, TUBA1B, TUBA1C, TUBB, TUBD1, TUBGCP2, TUBGCP4, TUFM, TUSC2, TUT1, TVP23B, TXLNA, TXLNG, TXN2, TXNDC11, TXNDC12, TXNDC15, TXNDC17, TXNDC9, TXNL1, TXNL4A, TXNL4B, TXNRD1, TYK2, TYW1, U2AF1, U2AF1L4, U2AF2, UAP1, UBA1, UBA2, UBA3, UBA5, UBA52, UBAC2, UBALD1, UBAP1, UBAP2L, UBB, UBC, UBE2A, UBE2B, UBE2D2, UBE2D3, UBE2D4, UBE2E1, UBE2E2, UBE2E3, UBE2F, UBE2G2, UBE2H, UBE2I, UBE2J1, UBE2J2, UBE2K, UBE2L3, UBE2M, UBE2N, UBE2NL, UBE2Q1, UBE2R2, UBE2V1, UBE2V2, UBE2W, UBE2Z, UBE3A, UBE3B, UBE3C, UBE4A, UBE4B, UBFD1, UBIAD1, UBL3, UBL4A, UBL5, UBL7, UBOX5, UBP1, UBQLN1, UBQLN2, UBQLN4, UBR2, UBR7, UBTD1, UBTF, UBXN2A, UBXN4, UBXN6, UCHL3, UCHL5, UCK1, UCK2, UCKL1, UEVLD, UFC1, UFD1L, UFL1, UFSP2, UGP2, UHRF1BPIL, ULK1, ULK3, UNC50, UNG, UPF1, UPF2, UPF3B, UPRT, UQCC, UQCR10, UQCR11, UQCRB, UQCRC1, UQCRC2, UQCRHL, UQCRQ, URGCP, URI1, URM1, UROD, UROS, USB1, USE1, USF1, USF2, USP10, USP14, USP16, USP19, USP22, USP25, USP27X, USP33, USP38, USP39, USP4, USP47, USP5, USP7, USP8, USP9X, UTP11L, UTP14A, UTP14C, UTP15, UTP23, UTP3, UTP6, UXS1, UXT, VAC14, VAMP3, VAMP5, VAPA, VAPB, VARS2, VBP1, VCP, VDAC3, VEZT, VIMP, VMA21, VPS16, VPS18, VPS25, VPS26A, VPS26B, VPS28, VPS29, VPS33A, VPS36, VPS37A, VPS4A, VPS51, VPS52, VPS53, VPS72, VRK2, VRK3, VTA1, VTI1A, VTI1B, WAC, WAPAL, WARS2, WBP11, WBP1L, WBP2, WBP4, WBSCR22, WDR1, WDR12, WDR13, WDR18, WDR20, WDR24, WDR25, WDR26, WDR3, WDR33, WDR36, WDR41, WDR43, WDR44, WDR45, WDR45B, WDR46, WDR55, WDR59, WDR5B, WDR6, WDR61, WDR70, WDR73, WDR74, WDR75, WDR77, WDR81, WDR830S, WDR85, WDR89, WDTC1, WIBG, WIPI2, WIZ, WRAP53, WRB, WRNIP1, WSB2, WTAP, WTH3D1, WWP1, WWP2, XIAP, XPA, XPC, XPNPEP1, XPO1, XPO7, XPOT, XRCC5, XRCC6, XYLT2, YAF2, YARS, YARS2, YIF1A, YIF1B, YIPF1, YIPF3, YIPF4, YIPF5, YIPF6, YKT6, YME11, YPEL2, YRDC, YTHDC1, YTHDF1, YTHDF2, YTHDF3, YWHAB, YWHAE, YY1, YY1AP1, ZADH2, ZBED4, ZBED6, ZBTB1, ZBTB10, ZBTB11, ZBTB14, ZBTB17, ZBTB18, ZBTB21, ZBTB25, ZBTB33, ZBTB39, ZBTB44, ZBTB45, ZBTB5, ZBTB6, ZBTB7A, ZBTB80S, ZC3H10, ZC3H11A, ZC3H13, ZC3H15, ZC3H18, ZC3H3, ZC3H7A, ZC3H7B, ZCCHC10, ZCCHC11, ZCCHC3, ZCCHC7, ZCCHC9, ZCRB1, ZDHHC14, ZDHHC16, ZDHHC2, ZDHHC3, ZDHHC4, ZDHHC5, ZDHHC8, ZFAND1, ZFAND2B, ZFAND3, ZFAND5, ZFAND6, ZFP91, ZFPL1, ZFR, ZFYVE1, ZFYVE19, ZFYVE27, ZGPAT, ZHX1, ZHX1-C80RF76, ZHX2, ZHX3, ZKSCAN1, ZMAT2, ZMAT3, ZMAT5, ZMPSTE24, ZMYM2, ZMYND11, ZNF121, ZNF131, ZNF134, ZNF138, ZNF142, ZNF143, ZNF146, ZNF174, ZNF181, ZNF189, ZNF195, ZNF197, ZNF207, ZNF22, ZNF226, ZNF232, ZNF24, ZNF259, ZNF274, ZNF277, ZNF280D, ZNF281, ZNF3, ZNF32, ZNF322, ZNF326, ZNF330, ZNF335, ZNF33A, ZNF343, ZNF347, ZNF37A, ZNF384, ZNF394, ZNF397, ZNF398, ZNF408, ZNF41, ZNF410, ZNF414, ZNF419, ZNF438, ZNF444, ZNF446, ZNF48, ZNF480, ZNF491, ZNF506, ZNF507, ZNF513, ZNF518A, ZNF526, ZNF561, ZNF574, ZNF576, ZNF579, ZNF580, ZNF592, ZNF593, ZNF598, ZNF620, ZNF622, ZNF623, ZNF638, ZNF639, ZNF641, ZNF644, ZNF649, ZNF654, ZNF655, ZNF664, ZNF668, ZNF672, ZNF687, ZNF688, ZNF691, ZNF7, ZNF706, ZNF721, ZNF740, ZNF76, ZNF764, ZNF770, ZNF777, ZNF787, ZNF805, ZNF814, ZNF830, ZNF865, ZNF91, ZNHIT1, ZNHIT3, ZNRD1, ZRANB1, ZRANB2, ZSCAN21, ZSCAN29, ZSCAN32, ZSWIM1, ZSWIM7, ZSWIM8, ZW10, ZXDA, ZXDB, and ZZZ3.

Preferably, the at least one reference genes is one or more of GAPDH, GUSB, HPRT1, and TBP. More preferably, the at least one reference genes includes at least each of GAPDH, GUSB, HPRT1, and TBP.

The present disclosure also describes kits useful for determining gene expression of a breast cancer sample and/or providing prognostic information to identify risk of recurrence. These kits comprise a set of probes and/or primers specific for the 3, 5, 9, 16, or 20 genes listed in Table 7 or Table 9. The kit may further comprise a computer readable medium.

In one embodiment of the present disclosure, the capture probes are immobilized on an array. By "array" is intended a solid support or a substrate with peptide or nucleic acid probes attached to the support or substrate. Arrays typically comprise a plurality of different capture probes that are coupled to a surface of a substrate in different, known locations. The arrays of the disclosure comprise a substrate having a plurality of capture probes that can specifically bind an intrinsic gene expression product. The number of capture probes on the substrate varies with the purpose for which the array is intended. The arrays may be low-density arrays or high-density arrays and may contain 4 or more, 8 or more, 12 or more, 16 or more, 32 or more addresses, but will minimally comprise probes for the 3, 5, 9, 16, or 20 genes listed in Table 7 or Table 9.

Techniques for the synthesis of these arrays using mechanical synthesis methods are described in, e.g., U.S. Pat. No. 5,384,261, incorporated herein by reference in its entirety for all purposes. The array may be fabricated on a surface of virtually any shape or even a multiplicity of surfaces. Arrays may be probes (e.g., nucleic-acid binding probes) on beads, gels, polymeric surfaces, fibers such as fiber optics, glass or any other appropriate substrate, see U.S. Pat. Nos. 5,770,358, 5,789,162, 5,708,153, 6,040,193 and 5,800,992, each of which is hereby incorporated in its entirety for all purposes. Arrays may be packaged in such a manner as to allow for diagnostics or other manipulation on the device. See, for example, U.S. Pat. Nos. 5,856,174 and 5,922,591, each of which is herein incorporated by reference.

In another embodiment, the kit comprises a set of oligonucleotide primers sufficient for the detection and/or quantitation of each of the 3, 5, 9, 16, or 20 genes listed in Table 7 or Table 9. The oligonucleotide primers may be provided in a lyophilized or reconstituted form, or may be provided as a set of nucleotide sequences. In one embodiment, the primers are provided in a microplate format, where each primer set occupies a well (or multiple wells, as in the case of replicates) in the microplate. The microplate may further comprise primers sufficient for the detection of one or more housekeeping genes as discussed infra. The kit may further comprise reagents and instructions sufficient for the amplification of expression products from the 3, 5, 9, 16, or 20 genes listed in Table 7 or Table 9.

In order to facilitate ready access, e.g., for comparison, review, recovery, and/or modification, the gene expressions are typically recorded in a database. Most typically, the database is a relational database accessible by a computational device, although other formats, e.g., manually accessible indexed files of expression profiles as photographs, analogue or digital imaging readouts, spreadsheets, etc. can be used. Regardless of whether the expression patterns initially recorded are analog or digital in nature, the expression patterns, expression profiles (collective expression patterns), and molecular signatures (correlated expression patterns) are stored digitally and accessed via a database. Typically, the database is compiled and maintained at a central facility, with access being available locally and/or remotely.

The methods described herein may be implemented and/or the results recorded using any device capable of implementing the methods and/or recording the results. Examples of devices that may be used include but are not limited to electronic computational devices, including computers of all types. When the methods described herein are implemented and/or recorded in a computer, the computer program that may be used to configure the computer to carry out the steps of the methods may be contained in any computer readable medium capable of containing the computer program. Examples of computer readable medium that may be used include but are not limited to diskettes, CD-ROMs, DVDs, ROM, RAM, and other memory and computer storage devices. The computer program that may be used to configure the computer to carry out the steps of the methods and/or record the results may also be provided over an electronic network, for example, over the internet, an intranet, or other network.

The present invention further comprises providing a subject in need a breast cancer treatment. The breast cancer treatment may include one or more anti-cancer or chemotherapeutic agents. Classes of anti-cancer or chemotherapeutic agents can include anthracycline agents, alkylating agents, nucleoside analogs, platinum agents, vinca agents, anti-estrogen drugs, aromatase inhibitors, ovarian suppression agents, endocrine/hormonal agents, bisphosphonate therapy agents and targeted biological therapy agents (e.g., antibodies). Specific anti-cancer or chemotherapeutic agents include cyclophosphamide, fluorouracil (or 5-fluorouracil or 5-FU), methotrexate, thiotepa, carboplatin, cisplatin, gemcitabine, anthracycline, taxanes, paclitaxel, protein-bound paclitaxel, doxorubicin, docetaxel, vinorelbine, tamoxifen, raloxifene, toremifene, fulvestrant, irinotecan, ixabepilone, temozolmide, topotecan, vincristine, vinblastine, eribulin, mutamycin, capecitabine, capecitabine, anastrozole, exemestane, letrozole, leuprolide, abarelix, buserlin, goserelin, megestrol acetate, risedronate, pamidronate, ibandronate, alendronate, denosumab, zoledronate, trastuzumab, tykerb or bevacizumab, or combinations thereof.

The treatment may include radiation therapy. Preferably, the treatment that includes radiation also includes cyclophosphamide, fluorouracil (or 5-fluorouracil or 5-FU), methotrexate, or combinations thereof. One such combination is CMF which includes cyclophosphamide, methotrexate, and fluorouracil; another such combination is AC which includes doxorubicin and cyclophosphamide.

The treatment may include a surgical intervention.

A "more aggressive" cancer treatment may comprise a higher dose of an anti-cancer or chemotherapeutic agent. A "more aggressive" cancer treatment may comprise more frequent dosing of an anti-cancer or chemotherapeutic agent. A "more aggressive" cancer treatment may comprise a more potent anti-cancer or chemotherapeutic agent. A "more aggressive" cancer treatment may comprise a plurality of anti-cancer or chemotherapeutic agents. A "more aggressive" cancer treatment may combine a plurality of treatment modalities, e.g., anti-cancer or chemotherapeutic agents along with surgical intervention, anti-cancer or chemotherapeutic agents along with radiation, radiation along with surgical intervention, and anti-cancer or chemotherapeutic agents, surgical intervention, and radiation. Any of the above-mentioned "more aggressive" cancer treatment may be combined with any other above-mentioned "more aggressive" cancer treatments or with other cancer treatments known in the art.

Unless otherwise defined, all technical and scientific terms used herein have the same meaning as commonly understood by one of ordinary skill in the art to which this invention belongs.

As used herein, the singular forms of a word also include the plural form of the word, unless the context clearly dictates otherwise; as examples, the terms "a," "an," and "the" are understood to be singular or plural and the term "or" is understood to be inclusive. By way of example, "an element" means one or more element.

The terms "one or more", "at least one", and the like are understood to include but not be limited to at least 1, 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150, 200, 300, 400, 500, 600, 700, 800, 900, 1000, 2000, 3000, 4000, 5000 or more and any number in between.

The terms "plurality", "at least two", "two or more", "at least second", and the like, are understood to include but not limited to at least 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150, 200, 300, 400, 500, 600, 700, 800, 900, 1000, 2000, 3000, 4000, 5000 or more and any number in between.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps.

About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Although methods and materials similar or equivalent to those described herein can be used in the practice or testing of the present invention, suitable methods and materials are described below. All publications, patent applications, patents, and other references mentioned herein are incorporated by reference in their entirety. The references cited herein are not admitted to be prior art to the claimed invention. In the case of conflict, the present Specification, including definitions, will control. In addition, the materials, methods, and examples are illustrative only and are not intended to be limiting.

Any of the above aspects and embodiments can be combined with any other aspect or embodiment as disclosed here in the Summary and/or in the Detailed Description sections, including the below Examples.

EXAMPLES

Example 1: Derivation of Stemprinter20, the Risk Score Based on the Complete Set of 20 Stem Cell Genes 1.1 Introduction With the aim of developing a more refined prognostic clinical tool for the evaluation of risk of distant recurrence in ER+/HER2− breast cancer patients, a quantitative real time-polymerase chain reaction (RT-qPCR) multi-gene assay, named StemPrintER20, which is based on the expression of twenty mammary stem cell (SC)-specific biomarkers, was developed. It was reasoned that given the central role of cancer stem cells (CSCs) in breast cancer tumorigenesis and progression, mammary SC-specific biomarkers might be particularly informative in terms of prediction of risk of recurrence.

To identify the SC-specific biomarkers, a global transcriptional profiling of human normal mammary stem cells (MaSCs) was performed, which produced a signature comprised of 2,306 Affymetrix probe sets, which is predictive of the biological, molecular and pathological features of human breast cancers. Using a bioinformatics approach allowed distillation of a refined "stemness signature" from the original MaSC profile. Briefly, the expression of probe sets upregulated in the MaSC profile in the public breast cancer gene expression dataset reported by Ivshina et al was analyzed. A group of 329 upregulated probe sets was identified that clearly distinguished between "SC-like" breast cancers, characterized by a negative clinical outcome, and "non-SC-like" breast cancers displaying a more favorable prognosis [HR=2.30 (1.50-3.59), P<0.0001]. The prognostic power of these 329 probe sets was confirmed in an independent breast cancer dataset [Pawitan et al. HR=3.69, (1.89-7.72), P<0.0001].

Towards the development of a genomic tool that could be incorporated into the clinical practice, the size of the 329-gene signature was further reduced by selecting the 20 genes that were the most highly and differentially expressed genes in "SC-like" poor prognosis breast cancers of the Ivshina dataset. Notably, the "restricted" 20-gene signature was as powerful as the 329-gene signature in predicting which patients were at high risk of developing distal metastases in the Ivshina et al. dataset [HR=2.82, (1.80-4.56), P<0.0001]. Moreover, in three independent datasets (Pawitan, and KI and GUYT from Loi), The 20 SC genes were observed to be overexpressed in tumors with poor clinical outcomes (FIG. 1A). Finally, the prognostic power of the 20-gene signature was compared with that of published breast cancer signatures using the TRANSBIG dataset, which has been used as a benchmark for the comparative analysis of the clinical validity of many recently published prognostic profiles. Only 15 of the 20 genes were present on the Affymetrix chips used in the TRANSBIG study, however, the expression pattern of these 15 genes alone was as powerful as other available prognostic signatures in predicting the risk of recurrence (entire patient follow-up period, >20 years) both in univariate and multivariable analyses (FIG. 1B).

1.2 Methods 1.2.1 Study Population

Information on all consecutive breast cancer patients operated at the European Institute of Oncology (Istituto Europeo di Oncologia: IEO) in Milan, Italy were systematically collected in a dedicated database and extracted data from the period 1997 to 2000. 1,827 ER+/HER2− breast cancer patients were identified who were operated during this period. Data were available regarding age, date at surgery, tumor characteristics (e.g., histological type, tumor size (pT), nodal involvement (pN), tumor grade, perivascular infiltration, Ki-67 status, estrogen receptor (ER) status, and progesterone receptor (PgR) status), and treatment modality (e.g., type of surgery, adjuvant radiotherapy, endocrine therapy, and chemotherapy).

The cohort of 1,827 patients was randomly split into one-third as the training set (N=609) and two-thirds as the validation set (N=1,218). The two sets were balanced for age and tumor characteristics (Table 1). The training set was used to develop the StemPrintER20 algorithm through penalized Cox modelling, by considering distant metastases as events. Distant metastasis events were defined as the time from surgery to the appearance of a distant metastasis or death from breast cancer as first event.

TABLE 1

| Clinico-pathological characteristics of ER+/HER2− patients included in the training and validation sets. | | | | |
|---|---|---|---|---|
| | Training set n = 609 | | Validation set n = 1218 | Fisher's exact test |
| | N | % | N | % | p-value |
| Age at surgery [years] | | | | | |
| mean ± SD | 54.2 ± 11.3 | | 54.3 ± 11.3 | | |
| median (Q1; Q3) | 53 (46; 62) | | 54 (46; 62) | | |
| min-max | 23-87 | | 25-93 | | |
| <50 | 217 | 35.6 | 453 | 37.2 | 0.54 |
| ≥50 | 392 | 64.4 | 765 | 62.8 | |

TABLE 1-continued

Clinico-pathological characteristics of ER+/HER2− patients included in the training and validation sets.

|  | Training set n = 609 | | Validation set n = 1218 | | Fisher's exact test |
|---|---|---|---|---|---|
|  | N | % | N | % | p-value |
| Menopausal status | | | | | |
| Premenopausal | 259 | 42.5 | 523 | 42.9 | 0.88 |
| Postmenopausal | 350 | 57.5 | 695 | 57.1 | |
| pT | | | | | |
| pT1 | 409 | 67.2 | 846 | 69.5 | 0.34 |
| pT2/3/4 | 200 | 32.8 | 372 | 30.5 | |
| pN | | | | | |
| pNx | 19 | 3.1 | 32 | 2.6 | 0.82 |
| pN0 | 303 | 49.8 | 607 | 49.8 | |
| pN+ | 287 | 47.1 | 579 | 47.5 | |
| Stage | | | | | |
| Early | 551 | 90.5 | 1112 | 91.3 | 0.74 |
| Advanced | 39 | 6.4 | 75 | 6.2 | |
| NA | 19 | 3.1 | 31 | 2.5 | |
| Tumor grade | | | | | |
| G1 | 140 | 23.0 | 278 | 22.8 | 0.56 |
| G2 | 291 | 47.8 | 619 | 50.8 | |
| G3 | 161 | 26.4 | 292 | 24.0 | |
| NA | 17 | 2.8 | 29 | 2.4 | |
| PgR status | | | | | |
| Pos | 503 | 82.6 | 1037 | 85.1 | 0.17 |
| Neg | 106 | 17.4 | 181 | 14.9 | |
| Ki-67 status | | | | | |
| >=14% | 396 | 65.0 | 803 | 65.9 | 0.81 |
| <14% | 213 | 35.0 | 414 | 34.0 | |
| NA | 0 | 0.0 | 1 | 0.1 | |
| HER2 status | | | | | |
| Neg | 534 | 87.7 | 1075 | 88.3 | 0.76 |
| NA | 75 | 12.3 | 143 | 11.7 | | pT, tumor size;
pN, lymph node involvement (pNx: unknown lymph node involvement, pN0: no positive lymph nodes, pN+: one or more positive lymph nodes);
PgR, progesterone receptor;
Pos, positive;
Neg, negative;
NA, not available.

1.2.2 Sample Preparation and Analysis
RNA Extraction and Quantitative Real-Time PCR For the PCR analysis, 1,827 formalin-fixed paraffin-embedded (FFPE) tissue blocks were assessed as suitable for RNA extraction. One tissue core of 1.5 mm in diameter or at least two 10 μm thick tissue sections (according to tumor size) were taken from each tissue block from a representative tumor area with adequate tumor cellularity (>60%), as selected by a pathologist.

Total RNA was extracted from the FFPE tissue samples using the AllPrep DNA/RNA FFPE Kit automated on QIAcube following manufacturer's instructions (Qiagen, Hilden, Germany). For mRNA analysis, 250 ng of total RNA (RNA concentration measured using the NanoDrop® ND-1000 Spectrophotometer) were reverse transcribed with random primers using the SuperScript® VILO™ cDNA Synthesis Kit (Thermo Fisher Scientific). To optimize the RT-qPCR expression analysis of the 20 genes of the signature from limited amounts of degraded RNA from FFPE tissues, probes were selected that target short regions (<100 bp in size) of the transcript to increase the probability of detection. A multiplex pre-amplification method designed for the dual purpose of stretching precious sample into more qPCR reactions and of improving the signal-to-noise ratio for the detection of low/moderate-abundance transcripts was also implemented. Therefore, following reverse transcription, cDNA was pre-amplified with the PreAMP Master Mix Kit (Thermo Scientific) for 10 cycles, following manufacturer's instructions, and diluted 1:25 prior to PCR analysis (5 μl were then used per PCR reaction, corresponding to 1 ng of cDNA).

Quantitative PCR was performed with hydrolysis probes (ThermoFisher Scientific) using the SsoAdvanced Universal Probes Supermix (Bio-Rad Laboratories) in 10 μl of final volume in 384-well plates. The PCR reaction was run in LightCycler (LC) 480 real-time PCR instruments (Roche) using the following thermal cycling conditions: 1 cycle at 95° C. for 30 sec, 45 cycles at 95° C. for 5 sec, and 60° C. for 30 sec.

TaqMan® gene expression assays were selected based on amplicon size (<100 bp), and on their ability to detect the Ref Seq identified in the Affymetrix meta-analysis and as many isoforms as possible. Custom TaqMan® assays (listed in Table 2) were designed, when possible, in the 3' region of the gene using the Primer Express Software V3.0 (ThermoFisher Scientific). The TaqMan® assays used for the PCR reactions are summarized in Table 2.

TABLE 2

Design details for each TaqMan® gene expression assay used in the PCR analysis.

| Gene Symbol | Assay ID | Ref Seq | Exon Boundary | Assay Location | Amplicon Length | Primer and Probe sequences |
|---|---|---|---|---|---|---|
| APOBEC3B | CUSTOM | NM_001270411.1 | 7 | 1095-1151 | 57 | Forward Primer: GGCTGCGGGCCATTC (SEQ ID NO: 1) Reverse Primer: CTTAGAGACTGAGGCCCA TCCTT (SEQ ID NO: 2) Probe-FAM: CCAGAATCAGGGAAAC (SEQ ID NO: 3) |
| RACGAP1 | CUSTOM | NM_001320007.1 | 17-18 | 1511-1578 | 68 | Forward Primer: TGTTACAGGACATCAAGC GTCAA (SEQ ID NO: 4) Reverse Primer: CCAATACTCCAGAGGCAA GGAA (SEQ ID NO: 5) |

TABLE 2-continued

Design details for each TaqMan® gene expression assay used in the PCR analysis.

| Gene Symbol | Assay ID | Ref Seq | Exon Boundary | Assay Location | Amplicon Length | Primer and Probe sequences |
|---|---|---|---|---|---|---|
| | | | | | | Probe-FAM: CCAAGGTGGTTGAGCG (SEQ ID NO: 6) |
| CENPW | CUSTOM | NM_001012507.3 | 2 | 664-724 | 61 | Forward Primer: CAAACGCTTGTGCGAGTA AATG (SEQ ID NO: 7) Reverse Primer: TTTGCTGCGGCCAGTACA (SEQ ID NO: 8) Probe-FAM: AGAGTCATTAACAAGGAG C (SEQ ID NO: 9) |
| H2AFZ | CUSTOM | NM_002106.3 | 1 | 501-559 | 59 | Forward Primer: GCTGGTGGTGGTGTCATT CC (SEQ ID NO: 10) Reverse Primer: TGTTGTCCTTTCTTCCCAA TCA (SEQIDNO: 11) Probe-FAM: CACATCCACAAATCT (SEQ ID NO: 12) |
| EXOSC4 | CUSTOM | NM_019037.2 | 3-4 | 432-499 | 69 | Forward Primer: GAAGCAGCCATCCTCACA CA (SEQ ID NO: 13) Reverse Primer: GCCTGTAGCACCTGCACA TAGA (SEQ ID NO: 14) Probe-FAM: ACCCACGCTCCCAGAT (SEQ ID NO: 15) |
| NOL3 | CUSTOM | NM_001276312.1 | 5 | 1428-1482 | 55 | Forward Primer: GCCCACCACGAGCATCA (SEQ ID NO: 16) Reverse Primer: CCTGGACTCCTAAGGGCA GAT (SEQ ID NO: 17) Probe-FAM: CCAGTCCTCAGCCC (SEQ ID NO: 18) |
| PHB | CUSTOM | NM_001281496.1 | 8 | 1176-1237 | 62 | Forward Primer: TCCACCTCCCTACCAAAA ATTG (SEQ ID NO: 19) Reverse Primer: CCCGAATTGGGACCTAAA GC (SEQ ID NO: 20) Probe-FAM: CAAGTGCCTATGCAAAC (SEQ ID NO: 21) |
| H2AFJ | CUSTOM | NM_177925.3 | 1 | 2131-2190 | 60 | Forward Primer: CAAAGGTCAGGCCGTACA CA (SEQ ID NO: 22) Reverse Primer: ACATCTCGAACCTGCCCA AT (SEQ ID NO: 23) Probe-FAM: CTCTGTTAGGAGGCAAAT (SEQ ID NO: 24) |
| SFN | CUSTOM | NM_006142.3 | 1 | 1115-1177 | 63 | Forward Primer: TGCCTCTGATCGTAGGAA TTGA (SEQ ID NO: 25) Reverse Primer: CCTGCCACTGTCCAGTTCT CA (SEQ ID NO: 26) Probe-FAM: TGTCCCGCCTTGTGG (SEQ ID NO: 27) |

TABLE 2-continued

Design details for each TaqMan® gene expression assay used in the PCR analysis.

| Gene Symbol | Assay ID | Ref Seq | Exon Boundary | Assay Location | Amplicon Length | Primer and Probe sequences |
|---|---|---|---|---|---|---|
| CDK1 | CUSTOM | NM_001786.4 | 2-3 | 164-239 | 76 | Forward Primer: GAGAAAATTGGAGAAGGT ACCTATGG (SEQ ID NO: 28) Reverse Primer: TCATGGCTACCACTTGAC CTGTA (SEQ ID NO: 29) Probe-FAM: TGTATAAGGGTAGACACA AAA (SEQ ID NO: 30) |
| EIF4EBP1 | Hs00607050_m1 | NM_004095.3 | 2-3 | 395 | 69 | Probe-FAM: ATAAGCGGGCGGGCGGTG AAGAGTC (SEQ ID NO: 31) |
| EPB41L5 | Hs01554426_m1 | NM 001184937.1 | 14-15 | 1375 | 67 | Probe-FAM: AACTTAGTGTTCACAATA ATGTTTC (SEQ ID NO: 32) |
| LY6E | Hs03045111_G1 | NM_001127213.1 | 3-4 | 329 | 66 | Probe-FAM: GCCGGCATTGGGAATCTC GTGACAT (SEQ ID NO: 33) |
| MIEN1 | Hs00260553_m1 | NM_032339.3 | 2-3 | 229 | 83 | Probe-FAM: CGGGGGCACAGGTGCCTT TGAGATA (SEQ ID NO: 34) |
| MMP1 | Hs00899658_m1 | NM 001145938.1 | 7-8 | 1019 | 64 | Probe-FAM: AAGTCCGGTTTTTCAAAG GGAATAA (SEQ ID NO: 35) |
| MRPS23 | Hs00950118_g1 | NM_016070.3 | 4-5 | 484 | 79 | Probe-FAM: AAGCAAGGACTCAACACG GAGGTAG (SEQ ID NO: 36) |
| NDUFB10 | Hs01018233_g1 | NM_004548.2 | 2-3 | 375 | 83 | Probe-FAM: AGTGGAAGAGGGACTACA AAGTCGA (SEQ ID NO: 37) |
| PHLDA2 | Hs04194980_s1 | NM_003311.3 | 1-1 | 254 | 75 | Probe-FAM: GCGCACGGGCAAGTACGT GTACTTC (SEQ ID NO: 38) |
| TOP2A | Hs01032142_g1 | NM_001067.3 | 26-27 | 3611 | 96 | Probe-FAM: TAAGAAATGAAAAAGAA CAAGAGCT (SEQ ID NO: 39) |
| ALYREF | Hs01099193_g1 | NM_005782.3 | 3-4 | 543 | 70 | Probe-FAM: CGTCCCTCTGGATGGCCG CCCCATG (SEQ ID NO: 40) |
| GAPDH | Hs03929097_g1 | NM_001256799.1 | 8-8 | 1250 | 58 | Probe-FAM: CAAGAGGAAGAGAGAGA CCCTCACT (SEQ ID NO: 41) |
| HPRT1 | Hs02800695_m1 | NM_000194.2 | 2-3 | 297 | 82 | Probe-FAM: GGACTAATTATGGACAGG ACTGAAC (SEQ ID NO: 42) |
| GUSB | Hs99999908_m1 | NM_000181.3 | 11-12 | 1925 | 81 | Probe-FAM: TGAACAGTCACCGACGAG AGTGCTG (SEQ ID NO: 43) |
| TBP | Hs00427621_m1 | NM_001172085.1 | 3-4 | 666 | 65 | Probe-FAM: AATCCCAAGCGGTTTGCT GCGGTAA (SEQ ID NO: 44) |

Gene name (Gene Symbol), Identification number (Assay ID) of each TaqMan assay, accession number of the transcripts (Ref Seq) recognized by the assay, exon boundary, assay location and amplicon length are indicated. For TaqMan custom assays, locations of 5' nucleotide start and 3' nucleotide end of the entire amplicon and oligonucleotide sequences of forward and reverse primers as well as FAM-probes are indicated. For proprietary designed TaqMan assays, locations corresponding to the nucleotide base located in the center of the probe and oligonucleotide context sequences of FAM-probes released by the vendor are reported.

For the RT-qPCR analysis, standard methods for RT-qPCR data mining and manufacturers' recommendations for quality control and sample rejection were used. Briefly, Cq=35 was defined as the limit of detection. Therefore, Cq values beyond this limit were set to 35 and normalization was omitted. Each target was assayed in triplicate and average Cq (AVG Cq) values were calculated either from triplicate values, when the standard deviation was <0.4, or from the best duplicate values when the standard deviation was >0.4. Data (AVG Cq) were normalized using four reference genes (HPRT1, GAPDH, GUSB, and TBP) to compensate for possible variations in the expression of single reference genes and in RNA integrity due to tissue fixation. The normalized Cq ($Cq_{normalized}$) of each target gene was calculated using the following formula:

$$Cq_{normalized} = AVG\ Cq - SF$$

where: SF is the difference between the AVG Cq value of the reference genes for each patient and a constant reference value K; K represents the mean of the AVG Cq of the four reference genes calculated across all samples (K=25.012586069). This normalization strategy allowed retention of information on the abundance of the original transcript, as measured by PCR (i.e., on the Cq scale), which is conversely lost when using the more classical ΔCq method. Normalized data were then processed for statistical analysis. Based on the distribution of the reference genes, The Tukey's interquartile rule was applied for outliers to identify poor quality RT-qPCR data. Based on this rule, no samples were excluded.

1.2.3 Development of the StemPrintER20 Algorithm

The ridge penalized Cox regression model was implemented on the training set considering the normalized gene expression of the 20 genes as continuous covariates with log-linear effect. Cross-Validated (10-fold) log-Likelihood (CVL) with optimization of the tuning penalty parameter was applied. Tuning of the penalty parameter was repeated 500 times using a different folding at each simulation and the model associated with the highest CVL was selected (Table 3).

TABLE 3

Development of the StemPrintER20 algorithm.

| Gene Symbol | Value |
|---|---|
| H2AFZ | −0.03833591325196550 |
| CDK1 | −0.06132455806571770 |
| EXOSC4 | −0.02105976326055420 |
| PHLDA2 | −0.06295739658169650 |
| APOBEC3B | 0.02341881674020150 |
| EIF4EBP1 | −0.13911217901125500 |
| SFN | 0.05788269046891110 |
| PHB | −0.03538557745953510 |
| EPB41L5 | −0.04675539403890050 |
| RACGAP1 | −0.05097505893853430 |
| MRPS23 | −0.14201022110072700 |
| TOP2A | −0.11290078348786600 |
| H2AFJ | −0.04975471358452700 |
| NOL3 | −0.04193802459521500 |
| MIEN1 | 0.01133668644106850 |
| CENPW | −0.03717918353187610 |
| LY6E | −0.02829256296234230 |
| ALYREF | −0.09541915699494330 |
| MMP1 | −0.00911370427072023 |
| NDUFB10 | 0.00626166874136819 |
| 2-class cut-off | |
| Median | 0.5631840823 |
| 3-class cut offs | |
| $33^{rd}$ percentile | 0.5014912809 |
| $66^{th}$ percentile | 0.6270727251 |
| Scale factors | |
| Maximum | −21.7767727 |
| Minimum | −25.2349961 |

Ridge penalized Cox regression model coefficients obtained from the training set are reported for each gene. Factors used to scale the risk score in a 0-1 range and cut-offs used to categorize patients into 2 classes (low, high) or 3 classes (low, intermediate, high) of risk are also reported.

A continuous risk score was assigned to each patient based on the following formula:

$$\text{Risk score} = \Sigma_i(\beta_i * Cq_{normalized})$$

where: i is the summation index for the 20 target genes; β is the ridge penalized Cox model coefficient for each target gene; $Cq_{normalized}$ is the normalized average Cq for each target gene. Minimum and maximum risk scores from the training set were used to scale risk scores in a 0-1 range. The median of the continuous risk score of the training set was used to identify two classes of risk (low and high). The $33^{rd}$ and $66^{th}$ percentiles were used to identify three classes of risk (low, intermediate, high: Table 3). The C-index was calculated as a measure of discrimination of the model, representing the probability of concordance between predicted and observed responses.

1.2.4 Sensitivity Analysis of the StemPrintER20 Algorithm

Figure 2:
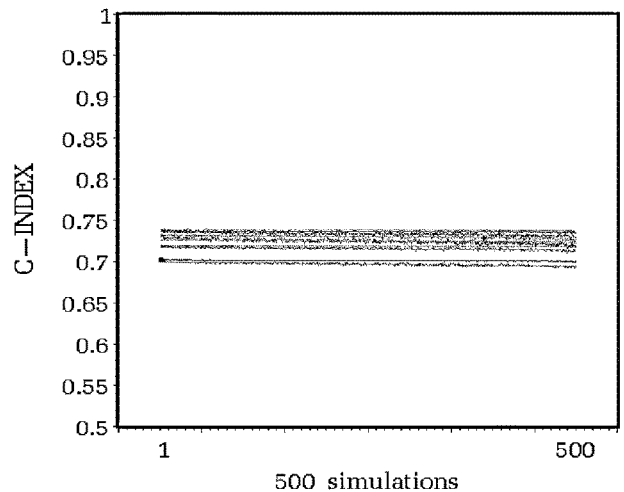
FIG. 2. C-index for the 5,000 models of the sensitivity analysis. Each line represents a different training set: blue lines=one-third as training; red lines=a half as training; green lines=two-thirds as training; black line=training set used for the development of the prognostic algorithm; and black dot=C-index for the prognostic algorithm considered.

A sensitivity analysis of the prognostic algorithm was performed by considering different scenarios based on nine different training sets. Specifically, three different ways of splitting the cohort to derive the training set were considered, based on a one-third (N=609), a half (N=914) or a two-thirds (N=1,218) split. For each split, three different random selections of patients were performed. The ridge penalized Cox regression model was implemented on each additional training set with the same method applied to the training cohort used for the development of the prognostic algorithm. Tuning of the penalty parameter was repeated 500 times using a different folding at each simulation. A total of 4,500 additional models were obtained from the sensitivity analysis. The C-index was calculated for each of the 4,500 additional models and compared to the 500 models obtained in the training cohort used for the development of the StemPrintER20 algorithm (Table 4 and FIG. 2).

TABLE 4

C-index of the sensitivity analysis.

| | C-index (95% CI) |
|---|---|
| Prognostic algorithm | 0.70 (0.65-0.75) |
| Min over 5,000 models | 0.69 (0.65-0.74) |
| Max over 5,000 models | 0.74 (0.70-0.78) |

The C-index value with the 95% confidence interval (95% CI) of the prognostic algorithm are reported. Minumum and maximum C-index values (and corresponding 95% CI) of the 5,000 models obtained in the sensiticity analysis are also reported.

1.3 Results

A continuous risk score to each patient of the training set based on the StemPrintER20 algorithm was assigned. A C-index of 0.70 (0.65-0.75) was obtained. Minimum and maximum C-index values obtained from the 5,000 models evaluated in the sensitivity analysis were 0.69 (0.65-0.74)

and 0.74 (0.70-0.78), respectively (Table 4). Based on the results of the sensitivity analysis, the StemPrintER20 algorithm was applied to estimate the crude and adjusted hazard ratios (HRs) for risk group classification in both the training and the validation sets.

Figure 3A:
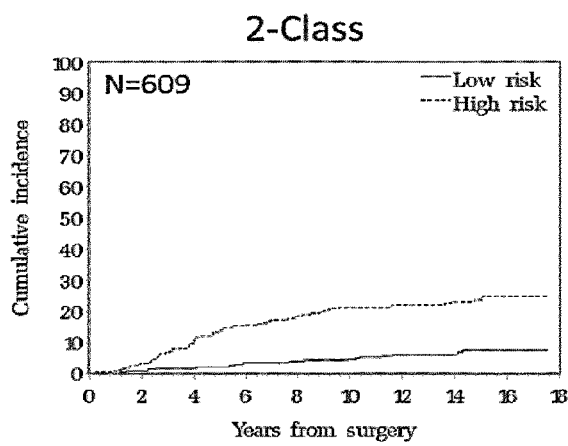
FIGS. 3A and 3B. Performance of the 2-class and 3-class StemPrintER20 risk models in the ER+/HER2− training set (N=609) of the European Institute of Oncology (Istituto Europeo di Oncologia: "IEO") cohort. The cumulative incidence of distant metastasis according to (FIG. 3A) the 2-class (based on the 50$^{th}$ percentile) and (FIG. 3B) the 3-class (based on $33_{rd}$ and 66$^{th}$ percentiles) risk models are shown. Hazard ratios (HR) for the high-risk group (HRHigh: 2-class and 3-class models) and intermediate-risk group (HRint: 3-class model), relative to the low-risk group, are reported with 95% CI.
Figure 3B:
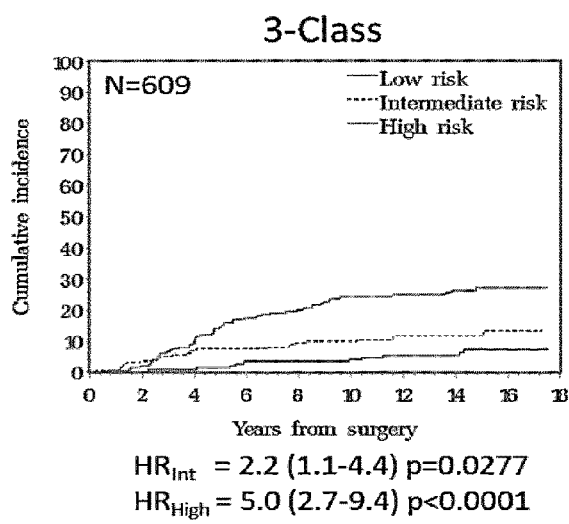

In the training set, with the 2-class risk model, HR was obtained for the high-risk group ($HR_{High}$)=4.2 (2.6-7.1), p<0.0001, relative to the low-risk group, while with the 3-class risk model, a $HR_{High}$=5.0 (2.7-9.4), p<0.0001 was obtained, and a HR for the intermediate-risk group ($HR_{Int.}$) =2.2 (1.1-4.4), p=0.0277 was obtained, relative to the low-risk group (FIG. 3). In the validation set, in a multivariable analysis (adjusted for pT, pN, tumor grade, Ki-67 and age), both risk models were observed to be predictive of prognosis over the entire follow-up period. With the 2-class risk model, a $HR_{High}$ vs. Low=1.9 (1.3-2.7), p=0.0019 was obtained, while with the 3-class risk model a $HR_{High}$ vs. Low=2.1 (1.3-3.6), p=0.0042 was obtained (FIGS. 4 and 5).

The ability of the 2- and 3-class risk models to predict early (<5 years from surgery) and late (5-10 years post-surgery) recurrence in the validation set was also determined. In a multivariable analysis (adjusted for pT, pN, tumor grade, Ki-67 and age), it was demonstrated that both the 2-class and 3-class risk models were predictive of early and late recurrence (FIGS. 4 and 5, Table 5). In addition, the continuous risk score based on a 10-unit increase, was also predictive of early and late recurrence in ER+/HER2− patients (Table 5). Using the continuous risk score, the cumulative incidence of events at 5 and at 10 years post-surgery for each risk group was determined. Notably, the 10-year cumulative incidence was estimated to be 5.8% and 4.5% in the low-risk groups derived from the 2-class and 3-class risk models, respectively (Table 6).

TABLE 6

Cumulative incidence of distant recurrence events at 5 years and at 10 years post-surgery stratified according to the StemPrintER20 2-class and 3-class risk models.

| Risk Model | 5-year Cumulative Incidence (95% CI) | 10-year Cumulative Incidence (95% CI) |
|---|---|---|
| 2-Class Low | 2.8% (1.7-4.4) | 5.8% (4.2-7.9) |
| 2-Class High | 12.3% (9.7-15.2) | 20.1% (16.9-23.6) |
| 3-Class Low | 2.6% (1.4-4.4) | 4.5% (2.8-6.8) |
| 3-Class Int. | 6.1% (4.0-8.7) | 11.1% (8.2-14.4) |
| 3-Class High | 14.1% (10.8-17.9) | 23.5% (19.3-28.0) |

Finally, the ability of the 2-class, 3-class and continuous risk models to predict risk of recurrence in specific patient subgroups: i.e., pre-menopausal and post-menopausal women, and lymph node negative (N0) and lymph node positive (N+) patients was assessed (Table 5). The StemPrintER20 algorithm was observed to be predictive of both early and late recurrence in pre-menopausal women. In post-menopausal women, the 2-class risk model was predictive of early recurrence. In N0 patients, all of the risk models were predictive of early recurrence, while in N+ patients, a statistically significant HR was obtained with the 2-class risk model for early recurrence, while all models yielded statistically significant HRs for late recurrence (Table 5).

Together, these results highlight the potential clinical value of the StemPrintER20 genomic predictor in the clinical management of ER+/HER2− BC patients, either as a

TABLE 5

Summary of the performance of the 2-class, 3-class and continuous (10-unit increase) StemPrintER20 risk models in predicting risk of recurrence in the time intervals 0-5 years and 5-10 years post-surgery in different patient subgroups of the ER+/HER2− validation set (N = 1,218).

| Patient Subgroup | N (events) | Risk Model | 0-5 y $HR_{High\ vs.\ Low}$ (95% CI) | P-value | 5-10 y $HR_{High\ vs.\ Low}$ (95% CI) | P-value |
|---|---|---|---|---|---|---|
| All ER+/HER2− patients | 1218 (163) | 2-Class | 2.6 (1.5-4.4) | 0.0009 | 1.9 (1.0-3.3) | 0.0377 |
| | | 3-Class | 2.5 (1.3-5.2) | 0.0096 | 2.8 (1.2-6.4) | 0.0137 |
| | | Continuous | 1.3 (1.1-1.5) | 0.0024 | 1.3 (1.1-1.5) | 0.0022 |
| Pre-menopausal | 523 (68) | 2-Class | 3.0 (1.1-7.8) | 0.0252 | 2.0 (0.9-4.7) | 0.10 |
| | | 3-Class | 2.7 (0.9-7.7) | 0.07 | 3.8 (1.2-12.1) | 0.0234 |
| | | Continuous | 1.4 (1.1-1.7) | 0.0126 | 1.5 (1.2-1.9) | 0.0012 |
| Post-menopausal | 695 (95) | 2-Class | 2.3 (1.2-4.5) | 0.0178 | 1.8 (0.8-4.0) | 0.18 |
| | | 3-Class | 2.4 (0.9-6.1) | 0.07 | 2.1 (0.6-6.7) | 0.22 |
| | | Continuous | 1.2 (0.995-1.5) | 0.0556 | 1.1 (0.8-1.4) | 0.59 |
| N0 | 607 (40) | 2-Class | 3.9 (1.2-12.2) | 0.0213 | 1.2 (0.3-4.1) | 0.81 |
| | | 3-Class | 6.5 (1.4-31.5) | 0.0194 | 1.9 (0.4-8.5) | 0.42 |
| | | Continuous | 1.7 (1.3-2.3) | 0.0006 | 1.4 (0.9-2.1) | 0.11 |
| N+ | 579 (121) | 2-Class | 2.3 (1.2-4.4) | 0.0121 | 2.0 (1.0-3.9) | 0.0424 |
| | | 3-Class | 2.0 (0.9-4.6) | 0.10 | 3.1 (1.1-8.4) | 0.0301 |
| | | Continuous | 1.2 (0.97-1.4) | 0.09 | 1.2 (1.0-1.5) | 0.0389 |

N, number of patients: in parentheses number of events for each subset of patients.

Hazard ratios (HR) for the high-risk group relative to the low-risk group ($HR_{High\ vs.\ Low}$) for the indicated models were calculated based on a multivariable analysis adjusted for pT, pN, tumor grade, Ki-67 and age (as appropriate).

standalone test or as a test to be used in combination with other genomic predictors and/or clinico-pathological parameters.

Example 2: Derivation of the Stemprinter3, Stemprinter9, and Stemprinter16 Risk Models from the Original Set of 20 Stem Cell Genes 2.1. Introduction In previous analyses, the StemPrintER5, a risk score based on a cluster of 5 SC genes that were able to recapitulate the prognostic power of all the 20 SC genes was identified. However, based on a number of reasons summarized in below Points 2A and 2B, an independent statistical methodology was employed, which also entails additional permutation steps (described in detail in below Sections 2.2.1 and 2.2.2) to obtain further refined algorithms starting from the original set of 20 SC genes. This procedure led to the identification of three new risk models, namely Stem-PrintER3, StemPrintER9, and StemPrintER16.

Point 2.A

For the generation of StemPrintER5, the ridge penalized Cox regression model considering the normalized gene expression of the original 20 SC genes as continuous covariates with log-linear effect was used. Cross-Validated (10-fold) log-Likelihood (CVL) with optimization of the tuning penalty parameter was applied. Tuning of the penalty parameter was repeated 500 times using a different folding at each simulation. This approach was implemented on a training set derived from the entire cohort of ER+/HER2− breast cancer patients (N=1,827) using a one-third split strategy (N=609), a procedure that originated a complementary set of 1,218 patients that were used for the validation cohort. From this analysis, StemPrintER5 was selected as the model associated with the highest CVL. StemPrintER5 was also the signature that appeared with highest frequency (36.8%) compared to all the other possible models (with a variable length ranging from 3 to 6 genes) that were present in the 500 simulations of the training set (Table 7).

TABLE 7

Comparison of the rate of occurrence of all the possible reduced signatures that can be derived set from the original set of 20 SC genes in the 500 simulations of a training set designed with a one-third split strategy.

| | SIGNATURE LENGTH | | | |
|---|---|---|---|---|
| GENE | 3 | 5 | 4 | 6 |
| EIF4EBP1 | X | X | X | X |
| TOP2A | X | X | X | X |
| MRPS23 | X | X | X | X |
| ALYREF | | X | X | X |
| PHLDA2 | | X | | X |
| H2AFJ | | | | X |
| FREQUENCY(%) | 162 (32.4%) | 184 (36.8%) | 150 (30%) | 4 (0.8%) |

The reduced signatures, with indicated lengths and rates of occurrence, identified by the ridge penalized Cox regression model in the 500 simulations of the same training set originally used for the development of StemPrintER20 are shown. The signature composed of 5 genes, which appears with a frequency of 36.8%, represents StemPrintER5.

However, in a retrospective analysis of the rate of occurrence of all the other models, a signature composed of 3 genes was noted and which represented the 'core' of all the other signatures identified in the permutation analysis, appearing with a frequency (32.4%) close to that of Stem-PrintER5 (Table 7). Based on this observation, it was reasoned that, by focusing on the strongest and immediately apparent best candidate, i.e., StemPrintER5, the relevance of other clusters of genes in terms of minimal requirement for optimal prognostication may have been underestimated.

Point 2.B

The StemPrintER5 risk model was developed using a training set derived from a one-third splitting of the entire ER+/HER2− breast cancer cohort. This approach is a well-established procedure for this type of study as it ensures, on the one hand, an adequate number of patients/events in the training set for the initial development of a robust risk model and, on the other hand, a sufficient number of patients/events for the independent validation of the performance of the risk score, thus avoiding overfitting in the analyses. Using this approach, which was identical to that used to derive StemPrintER20 (see above Section 1.2.3), it was possible to validate StemPrintER5 and also to perform a direct comparison of StemPrintER5 and StemPrintER20 in the very same validation set of 1,218 patients (see Example 1, Results Sections 1.3 and 1.4 for StemPrintER20; results for StemPrintER5: data not shown).

This notwithstanding, whether the use of training cohorts of different dimensions could have an impact on the size of the minimal cluster of genes required for optimal prognostication was checked. With this idea in mind, irrespective of the necessity to have an independent set of patients for the validation analysis, different splitting strategies to yield training sets of different dimensions from the whole cohort was used. To this aim, in addition to the one-third split strategy used in a previous analysis, also considered was a two-thirds split strategy and a strategy based on the entire cohort of 1,827 patients to design training sets for the derivation of a reduced prognostic signature from the original cluster of 20 SC genes (see below Sections 2.2.1 and 2.2.2 for a detailed description of these procedures). The results of this new approach (see below Sections 2.3 and 2.4) show that increasing the number of patients used for the initial training of the risk score does influence the size of the optimal minimal number of genes identified by the Lasso penalized Cox regression model. A plausible biological explanation for this phenomenon is that breast tumors are highly heterogeneous, a notion that can be extended to their intrinsic sternness nature, and therefore increasing the number of breast tumors in a given cohort may require more genes to describe the inter-tumor variability of sternness phenotypes. With regards to translation into practice, the possibility exists that different clusters of stem genes may better stratify specific subsets of ER+/HER2− breast cancer patients based on their intrinsic sternness characteristics (for instance pre- vs. post-menopausal, or node-negative vs. node-positive patients).

Herein, is described the stepwise methodology used to identify three new risk models, StemPrintER3, StemPrintER9 and StemPrintER16, which represent the best performing "daughter" risk models that can be derived from the original set of the 20 SC genes that comprise the "mother" StemPrintER20.

2.2. Methods.

2.2.1. Study Population

The entire cohort of ER+/HER2− breast cancer patients is described in detail above in Example 1, Section 1.2.1.

For the identification of the training sets, three different cohort splits were used, considering one-third (N=609) or two-thirds (N=1,218) of patients, or the entire cohort (N=1,827), as training sets. Three different random selections were performed for each split. Considering all the complementary datasets, this approach generated 15 different training sets (7 different "one-third" datasets, 7 different "two-thirds" datasets plus one dataset corresponding to the entire population).

2.2.2. Procedure for the Identification of a Reduced Signature

The Lasso penalized Cox regression model was implemented on the training set considering the normalized gene expression of the 20 genes as continuous covariates with log-linear effect. Cross-Validated (10-fold) log-Likelihood (CVL) with optimization of the tuning penalty parameter was applied. Tuning of the penalty parameter was repeated 1,000 times using a different folding at each simulation, for a total of 15,000 simulations across the different training sets.

Figures 6A, 6B:
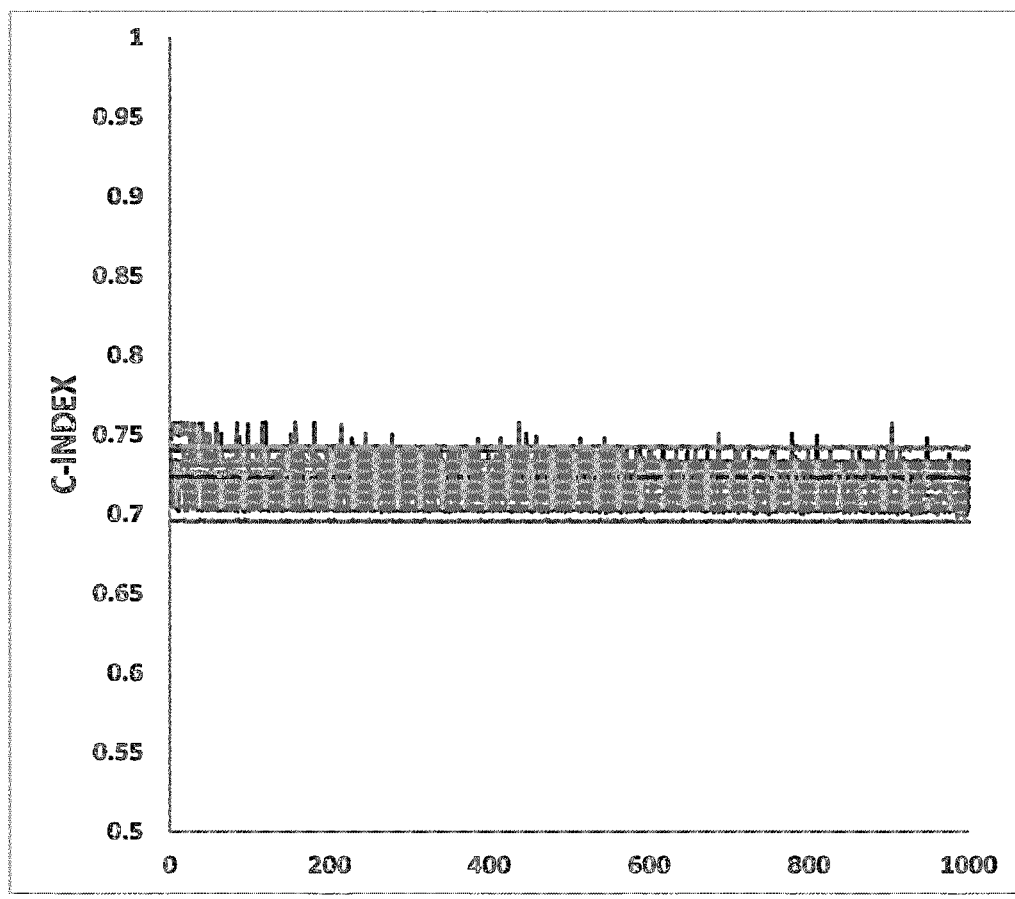
FIGS. 6A and 6B. Comparative analysis of the C-index relative to each of the 15,000 models generated from the 15 different training sets.

A continuous risk score was assigned to each patient based on the following formula:

$$\text{Risk score} = \Sigma_i (\beta_i * Cq_{normalized})$$

where: i is the summation index for the identified target genes; β is the Lasso penalized Cox model coefficient for each target gene; $Cq_{normalized}$ is the normalized average Cq for each target gene. The C-index was calculated as a measure of discrimination of the model, representing the probability of concordance between predicted and observed responses. The outcome of this process was the generation of 15,000 different signatures (1,000 different signatures/dataset). In an attempt to identify the minimal signature associated with the strongest prognostic power across the 15 different training sets, a two-fold approach was used:

i) a comparative analysis of the C-index associated to each of the 15,000 signatures (FIG. 6).

ii) a careful analysis of frequency at which signatures with varying lengths appeared in the different training splits (Table 8).

TABLE 8

Analysis of the distribution of signature lengths by dataset size.

| Signature Length | Total N | Total % | 33% N | 33% % | 66% N | 66% % | Entire cohort N | Entire cohort % |
|---|---|---|---|---|---|---|---|---|
| 2 | 1 | 0.0 | 1 | 0.0 | 0 | 0.0 | 0 | 0.0 |
| 3 | 346 | 1.7 | 346 | 4.9 | 0 | 0.0 | 0 | 0.0 |
| 4 | 317 | 1.5 | 310 | 4.4 | 0 | 0.0 | 0 | 0.0 |
| 5 | 1980 | 9.4 | 942 | 13.5 | 0 | 0.0 | 0 | 0.0 |
| 6 | 2454 | 11.7 | 1609 | 23.0 | 12 | 0.2 | 0 | 0.0 |
| 7 | 1197 | 5.7 | 545 | 7.8 | 533 | 7.6 | 0 | 0.0 |
| 8 | 1197 | 5.7 | 607 | 8.7 | 484 | 6.9 | 0 | 0.0 |
| 9 | 2132 | 10.2 | 1845 | 26.4 | 20 | 0.3 | 0 | 0.0 |
| 10 | 1000 | 4.8 | 154 | 2.2 | 20 | 0.3 | 0 | 0.0 |
| 11 | 640 | 3.1 | 67 | 1.0 | 400 | 5.7 | 0 | 0.0 |
| 12 | 234 | 1.1 | 2 | 0.0 | 130 | 1.9 | 0 | 0.0 |
| 13 | 762 | 3.6 | 135 | 1.9 | 564 | 8.1 | 0 | 0.0 |
| 14 | 1545 | 7.4 | 5 | 0.1 | 1470 | 21.0 | 1 | 0.1 |
| 15 | 2322 | 11.1 | 17 | 0.2 | 1165 | 16.6 | 47 | 4.7 |
| 16 | 2781 | 13.2 | 22 | 0.3 | 1303 | 18.6 | 814 | 81.4 |
| 17 | 1501 | 7.2 | 297 | 4.2 | 898 | 12.8 | 134 | 13.4 |
| 18 | 576 | 2.7 | 96 | 1.4 | 1 | 0.0 | 4 | 0.4 |
| 19 | 15 | 0.1 | 0 | 0.0 | 0 | 0.0 | 0 | 0.0 |
| | 15000 | 100 | 7000 | 100 | 7000 | 100 | 1000 | 100 |

The frequency at which signatures with different lengths appear in each of the different training sets, obtained using a one-third (33%) or a two-third (66%) split, or based on the entire cohort are reported.
The signatures with the highest frequency of occurrence in each dataset are indicated in bold.

Neither approach was able to identify a reduced signature that was superior to all the others, as demonstrated by results showing that: i) all the 15,000 models displayed a statistically equivalent prognostic power, when a stringent approach (p<0.01) to evaluate the C-index variations across all the models was used (FIG. 6); ii) it was not possible to identify a reduced signature with a predominant frequency in any of the different datasets (Table 8). One important exception was a signature composed of 16 genes that appeared with a frequency of more than 80% in the training set composed of the entire patient cohort (Table 8).

An analysis of the frequency of occurrence of each of the 20 SC genes, considered individually, across the different simulations obtained for each training dataset (7,000 for one-third, 7,000 for two-thirds and 1,000 for the entire cohort) was therefore conducted. Using a threshold of 80% to select the largest cluster of genes most highly represented in each split, a minimal cluster of 3 genes (TOP3) for the training sets based on a one-third split, 9 genes (TOP9) for the training sets based on a two-thirds split and 16 genes (TOP16) for the training sets based on the entire cohort was identified (FIG. 7, top panel). When considered as a whole, these three signatures were represented in more than 80% of the simulations of their respective datasets: TOP3 in 85.7% of the one-third datasets, TOP9 in 84.2% of the two-thirds datasets, TOP16 in 95.2% of the simulations performed on the entire cohort (FIG. 7, bottom panel). Importantly, this analysis showed that the length of the reduced signature is heavily influenced by the size of the cohort used for the training analysis.

2.2.3. Derivation of StemPrintER3, StemPrintER9 and StemPrintER16

TOP3, TOP9, and TOP16 represented the starting point for the derivation of StemPrintER3, StemPrintER9, and StemPrintER16, i.e., the risk scores associated with these three different signatures. Using an approach identical to the derivation of StemPrintER20 (see above Section 1.2.3), the ridge penalized Cox regression model on each of the different training sets was implemented, considering the normalized gene expression of the identified genes (TOP3, TOP9 and TOP16) as continuous covariates with log-linear effect. Cross-Validated (10-fold) log-Likelihood (CVL) with optimization of the tuning penalty parameter was applied. Tuning of the penalty parameter was repeated 500 times using a different folding at each simulation and the model associated with highest CVL was selected.

A continuous risk score was assigned to each patient based on the following formula:

$$\text{Risk score} = \Sigma_i (\beta_i * Cq_{normalized})$$

where: i is the summation index for the identified target genes; β is the ridge penalized Cox model coefficient for each target gene; $Cq_{normalized}$ is the normalized average Cq for each target gene. Minimum and maximum risk scores from the training sets were used to scale risk scores in a 0-1 range. Median of the continuous risk score of the training set was used to identify 2 classes of risk (low, high). The $33^{rd}$ and $66^{th}$ percentiles were used to identify 3 classes of risk (low, intermediate, high; Table 9).

TABLE 9

Development of StemPrintER3, StemPrintER9 and StemPrintER16 algorithms.

| Gene Symbol | StemPrintER3 Value | StemPrintER9 Value | StemPrintER16 Value |
|---|---|---|---|
| H2AFZ | | | |
| CDK1 | | | −0.0777226352877493 |
| EXOSC4 | | 0.3440660812818810 | 0.2571414958102690 |
| PHLDA2 | | | |
| APOBEC3B | | 0.2110001016524630 | 0.2027825590936980 |
| EIF4EBP1 | −0.2661522777700890 | −0.2223133616036320 | −0.2329055344285050 |
| SFN | | | 0.0591955291393095 |
| PHB | | | |
| EPB41L5 | | | |
| RACGAP1 | | | −0.0928937254771330 |
| MRPS23 | −0.4064807990811070 | −0.4788624802373240 | −0.4265118770613120 |
| TOP2A | −0.1898759903565910 | −0.2406479942640310 | −0.1515759123771920 |
| H2AFJ | | | −0.0432973988579006 |
| NOL3 | | | −0.1044402373747570 |
| MIEN1 | | | 0.0607555452253983 |
| CENPW | | −0.2053740290368180 | −0.1260999729121140 |
| LY6E | | −0.2897586785096140 | −0.2129142199263660 |
| ALYREF | | | −0.0867101647370881 |
| MMP1 | | −0.0824402740633608 | −0.0499993277954095 |
| NDUFB10 | | 0.3085837868590590 | 0.2355873243333520 |
| 2-class cut-off | | | |
| Median | 0.5764232049 | 0.5846205237 | 0.5006739155 |
| 3-class cut offs | | | |
| 33$^{rd}$ percentile | 0.5203796368 | 0.5400223537 | 0.4524096153 |
| 66$^{th}$ percentile | 0.6282780877 | 0.6367800051 | 0.5568569152 |
| Scale factors | | | |
| Maximum | −25.7042450 | −20.7862332 | −23.2258647 |
| Minimum | −20.9745943 | −14.1818678 | −17.5699641 |

Ridge penalized Cox regression model coefficients obtained from the training set are reported for each gene. Factors used to scale the risk score in a 0-1 range and cut-offs used to categorize patients into 2 classes (low, high) or 3 classes (low, intermediate, high) of risk are also reported.

2.3. Results

A continuous risk score to each patient of the training set based on the StemPrintER3, StemPrintER9 and StemPrintER16 algorithms was assigned. The StemPrintER3, StemPrintER9 and StemPrintER16 algorithms to estimate the crude and adjusted hazard ratios (HRs) for risk group classification in the training sets was applied. Since StemPrintER16 was derived from a training set based on the entire cohort, a validation analysis with this algorithm could not be performed. Therefore, only StemPrintER3 and StemPrintER9, derived respectively from datasets based on a one-third and two-thirds split, could be used for validation analyses using their complementary datasets. The median of the continuous risk score of the training set was used to identify 2 classes of risk (low, high). The 33$^{rd}$ and 66$^{th}$ percentiles were used to identify 3 classes of risk (low, intermediate, high).

In a univariate analysis with the 2-class risk models, the HR for the high-risk group, relative to the low-risk group, was 4.0 (2.4-6.6), p<0.0001 for StemPrintER3, 4.6 (3.1-6.7), p<0.0001 for StemPrintER9 and 3.6 (2.7-4.8), p<0.0001 for StemPrintER16 (Table 10). With the 3-class risk model, the following results were obtained (Table 10):

TABLE 10

Summary of the performance of the 2-class, 3-class and continuous (10-unit increase) StemPrintER3, StemPrintER9 and StemPrintER16 risk models in predicting risk of recurrence in the training set. Univariate analysis.

| Risk Model | StemPrintER3 N = 609 | | StemPrintER9 N = 1218 | | StemPrintER16 N = 1827 | |
|---|---|---|---|---|---|---|
| | HR (95% CI) | p-value | HR (95% CI) | p-value | HR (95% CI) | p-value |
| 2-Class: High vs Low | 4.0 (2.4-6.6) | <0.0001 | 4.6 (3.1-6.7) | <0.0001 | 3.6 (2.7-4.8) | <0.0001 |
| 3-Class: Int vs Low | 2.0 (1.0-4.1) | 0.0451 | 1.8 (1.1-3.1) | 0.027 | 2.3 (1.5-3.6) | 0.00013 |
| 3-Class: High vs Low | 5.0 (2.7-9.4) | <0.0001 | 6.1 (3.8-9.8) | <0.0001 | 6.2 (4.2-9.2) | <0.0001 |
| Continuous risk score | 1.6 (1.4-1.9) | <0.0001 | 2.0 (1.8-2.3) | <0.0001 | 1.8 (1.7-2.0) | <0.0001 |

Finally, using the continuous risk score, the cumulative incidence of events at 5 and at 10 years post-surgery for each risk group using the 3-class risk model of StemPrintER3, StemPrintER9, and StemPrintER16 was determined. Notably, it was estimated that the 10-year cumulative incidence was very similar in the high-risk groups derived from the 3-class risk models [23.9% (18.2-30.1) for StemPrintER3, 25.0% (20.8-29.4) for StemPrintER9 and 24.5% (21.1-28.1) for StemPrintER16] (Table 11). Similar results were obtained, in terms of 10-year cumulative incidence, for the low-risk groups identified by the three different predictors [4.1% (1.9-7.6) for StemPrintER3, 4.4% (2.6-6.7) for StemPrintER9 and 3.9% (2.6-5.7) for StemPrintER16] (Table 11). Together, these results highlight the potential clinical value of these three genomic predictors in the clinical management of ER+/HER2– patients. However, an extensive comparative analysis in large clinical cohorts is required to compare the clinical value of these three genomic predictors with that of StemPrintER20.

TABLE 11

Cumulative incidence of distant recurrence events at 5 years and at 10 years post-surgery stratified according to the StemPrintER3, StemPrintER9 and StemPrintER16 3-class risk models.

| Risk Model | 5-year Cumulative Incidence (95% CI) | 10-year Cumulative Incidence (95% CI) |
| --- | --- | --- |
| StemPrintER3 | | |
| 3-Class Low | 2.0% (0.7-4.8) | 4.1% (1.9-7.6) |
| 3-Class Int. | 8.0% (4.7-12.2) | 10.5% (6.7-15.2) |
| 3-Class High | 13.6% (9.3-18.7) | 23.9% (18.2-30.1) |
| StemPrintER9 | | |
| 3-Class Low | 2.3% (1.1-4.1) | 4.4% (2.6-6.7) |
| 3-Class Int. | 3.7% (2.2-6.0) | 8.2% (5.8-11.2) |
| 3-Class High | 15.8% (12.4-19.6) | 25.0% (20.8-29.4) |
| StemPrintER16 | | |
| 3-Class Low | 2.0% (1.1-3.4) | 3.9% (2.6-5.7) |
| 3-Class Int. | 4.8% (3.3-7.0) | 9.4% (7.2-11.9) |
| 3-Class High | 15.5% (12.7-18.5) | 24.5% (21.1-28.1) |

In the validation set, in a multivariable analysis adjusted for pT, pN, tumor grade, Ki-67 and age, the StemPrintER3 continuous risk score, based on a 10-unit increase, was observed to be predictive of prognosis over the entire follow-up period [HR=1.3 (1.1-1.5), p=0.0009 (Table 12). The StemPrintER3 continuous risk score was also predictive of early and late recurrence [HR<5 years=1.3 (1.1-1.5), p=0.0022; HR 5-10 years=1.3 (1.1-1.6), p=0.0091](Table 12). Of note, the performance of the continuous risk scores of StemPrintER3 and StemPrintER9 were very similar in univariate analyses (Table 12). In the multivariable analyses, although very similar to those calculated with StemPrintER3, the HRs obtained with the StemPrintER9 continuous risk score for the entire follow-up [HR=1.2 (1.0-1.5), p=0.0896], and for early and late risk of recurrence [HR<5 years=1.3 (1.0-1.7), p=0.0591; HR 5-10 years=1.2 (0.9-1.7), p=0.231] were not statistically significant (Table 12). However, a careful analysis of the confidence intervals and p values associated with the HRs of the StemPrintER9 continuous risk score revealed that these results are likely to be attributed to the relatively small size of the dataset (one-third of the entire cohort) available for the validation of StemPrintER9.

TABLE 12

Summary of the performance of the continuous (10-unit increase) StemPrintER3 and StemPrintER9 risk models in predicting risk of recurrence in the validation set.

| | StemPrintER3 N = 1218 | | StemPrintER9 N = 609 | |
| --- | --- | --- | --- | --- |
| Risk Model | HR (95% CI) | p-value | HR (95% CI) | p-value |
| Univariate | | | | |
| Any time | 1.6 (1.5-1.8) | <0.0001 | 1.6 (1.4-1.9) | <0.0001 |
| <5 years | 1.7 (1.4-1.9) | <0.0001 | 1.7 (1.4-2.1) | <0.0001 |
| 5-10 years | 1.7 (1.4-2.0) | <0.0001 | 1.7 (1.3-2.3) | <0.0001 |
| Multivariable* | | | | |
| Any time | 1.3 (1.1-1.5) | 0.0009 | 1.2 (1.0-1.5) | 0.0896 |
| <5 years | 1.3 (1.1-1.5) | 0.0022 | 1.3 (1.0-1.7) | 0.0591 |
| 5-10 years | 1.3 (1.1-1.6) | 0.0091 | 1.2 (0.9-1.7) | 0.231 |

N, number of patients.
Multivariable analysis adjusted for pT, pN, tumor grade, Ki-67 and age (as appropriate).

REFERENCES

Nadji, M., Gomez-Fernandez, C., Ganjei-Azar, P. & Morales, A. R. Immunohistochemistry of estrogen and progesterone receptors reconsidered: experience with 5,993 breast cancers. *Am J Clin Pathol* 123, 21-27 (2005).

Sorlie, T. et al. Gene expression patterns of breast carcinomas distinguish tumor subclasses with clinical implications. *Proc Natl Acad Sci USA* 98, 10869-10874, doi: 10.1073/pnas.191367098 (2001).

Goldhirsch, A. et al. Personalizing the treatment of women with early breast cancer: highlights of the St Gallen International Expert Consensus on the Primary Therapy of Early Breast Cancer 2013. *Ann Oncol* 24, 2206-2223, doi:10.1093/annonc/mdt303 (2013).

Davies, C. et al. Long-term effects of continuing adjuvant tamoxifen to 10 years versus stopping at 5 years after diagnosis of oestrogen receptor-positive breast cancer: ATLAS, a randomised trial. *Lancet* 381, 805-816, doi: 10.1016/S0140-6736(12)61963-1 (2013).

Geffen, D. B. et al. The impact of the 21-gene recurrence score assay on decision making about adjuvant chemotherapy in early-stage estrogen-receptor-positive breast cancer in an oncology practice with a unified treatment policy. *Ann Oncol* 22, 2381-2386, doi:10.1093/annonc/mdq769 (2011).

Katz, S. J. & Morrow, M. Addressing overtreatment in breast cancer: The doctors' dilemma. *Cancer* 119, 3584-3588, doi:10.1002/cncr.28260 (2013).

Visvader, J. E. & Lindeman, G. J. Cancer stem cells in solid tumours: accumulating evidence and unresolved questions. *Nat Rev Cancer* 8, 755-768, doi:10.1038/nrc2499 (2008).

Zhou, J. & Zhang, Y. Cancer stem cells: Models, mechanisms and implications for improved treatment. *Cell Cycle* 7, 1360-1370 (2008).

Pece, S. et al. Biological and molecular heterogeneity of breast cancers correlates with their cancer stem cell content. *Cell* 140, 62-73, doi:10.1016/j.cell.2009.12.007 (2010).

Ivshina, A. V. et al. Genetic reclassification of histologic grade delineates new clinical subtypes of breast cancer. *Cancer Res* 66, 10292-10301, doi:10.1158/0008-5472.CAN-05-4414 (2006).

Pawitan, Y. et al. Gene expression profiling spares early breast cancer patients from adjuvant therapy: derived and validated in two population-based cohorts. *Breast Cancer Res* 7, R953-964, doi:10.1186/bcr1325 (2005).

Loi, S. et al. Predicting prognosis using molecular profiling in estrogen receptor-positive breast cancer treated with tamoxifen. *BMC Genomics* 9, 239, doi:10.1186/1471-2164-9-239 (2008).

Desmedt, C. et al. Strong time dependence of the 76-gene prognostic signature for node-negative breast cancer patients in the TRANSBIG multicenter independent validation series. *Clin Cancer Res* 13, 3207-3214, doi:10.1158/1078-0432.CCR-06-2765 (2007).

Haibe-Kains, B. et al. Comparison of prognostic gene expression signatures for breast cancer. *BMC Genomics* 9, 394, doi:10.1186/1471-2164-9-394 (2008).

Hudis, C. A. et al. Proposal for standardized definitions for efficacy end points in adjuvant breast cancer trials: the STEEP system. *J Clin Oncol* 25, 2127-2132, doi:10.1200/JCO.2006.10.3523 (2007).

Tukey, J. W. *Exploratory Data Analysis*. 43-44 (Addison-Wesley, 1977).

Hoerl A. E., Kennar R. W. Ridge regression: biased estimation for nonorthogonal problems. *Technometrics* 12, 55-67, doi:10.2307/1267351 (1970).

van Wieringen W N, Kun D, Hampel R, Boulesteix A L. Survival prediction using gene expression data: A review and comparison. *Comput Stat Data An* 53, 1590-1603, doi:10.1016/j.csda.2008.05.021 (2009).

Waldron L, Pintilie M, Tsao M S, Shepherd F A, Huttenhower C, Jurisica I. Optimized application of penalized regression methods to diverse genomic data. *Bioinformatics* 27, 3399-3406, doi:10.1093/bioinformatics/btr591 (2011).

Harrell, F. E., Jr., Lee, K. L. & Mark, D. B. Multivariable prognostic models: issues in developing models, evaluating assumptions and adequacy, and measuring and reducing errors. *Stat Med* 15, 361-387, doi:10.1002/(SICI)1097-0258(19960229)15:4<361::AID-SIM168>3.0.CO;2-4 (1996).

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating a human subject having breast cancer comprising steps of:
   (a) determining, in a breast tissue or breast cell sample from the subject the expression of a group of genes;
   (b) calculating a risk score based upon the expression of the group of genes, wherein a higher risk score indicates an increased risk of breast cancer recurrence in the subject, wherein the risk score is calculated according to the following formula:

Risk score=$\Sigma i(\beta i * Cq_{normalized})$, wherein $Cq_{normalized}$ is calculated according to the following formula:

$Cq_{normalized}$=AVG $Cq$-SF, wherein SF is the difference between the AVG Cq value of at least one reference gene for each subject and a constant reference value K, wherein K=25.012586069, which represents the mean of the AVG Cq of the at least one reference gene calculated across a plurality of training samples;
   (c) stratifying the subject into a high or low risk group; and
   (d) administering a breast cancer treatment to the subject, wherein a subject stratified in a high risk group is provided a cancer treatment that is more aggressive than the cancer treatment provided to a subject stratified in a low risk group;
   wherein said group of genes consists of:
   (i) EIF4EBP1, MRPS23, and TOP2A;
   (ii) APOBEC3B, CENPW, EIF4EBP1, EXOSC4, LY6E, MMP1, MRPS23, NDUFB10, and TOP2A;
   (iii) ALYREF, APOBEC3B, CDK1, CENPW, EIF4EBP1, EXOSC4, H2AFJ, LY6E, MIEN1, MMP1, MRPS23, NDUFB10, NOL3, RACGAP1, SFN, and TOP2A; or
   (iv) H2AFZ, CDK1, EXOSC4, PHLDA2, APOBEC3B, EIF4EBP1, SFN, PHB, EPB41L5, RACGAP1, MRPS23, TOP2A, H2AFJ, NOL3, MIEN1, CENPW, LY6E, ALYREF, MMP1, and NDUFB10.

2. The method of claim 1, wherein the at least one reference gene is selected from the group consisting of GAPDH, GUSB, HPRT1, and TBP.

3. The method of claim 1, wherein the gene expression is determined using reverse transcription and real-time quantitative polymerase chain reaction (RT-qPCR) with primers and/or probes specific for each gene of the said group of genes.

4. The method of claim 1, wherein the sample is a breast tumor obtained from the subject, a cancerous cell obtained from the subject, or a breast cancer stem cell obtained from the subject.

5. The method of claim 1, wherein the breast cancer treatment comprises surgery, radiation, anthracycline agents, alkylating agents, nucleoside analogs, platinum agents, vinca agents, anti-estrogen drugs, aromatase inhibitors, ovarian suppression agents, endocrine/hormonal agents, bisphophonate therapy agents, targeted biological therapy agents, and antibodies, or combinations thereof.

6. The method of claim 1, wherein the cancer treatment comprises cyclophosphamide, fluorouracil, 5-fluorouracil, methotrexate, thiotepa, carboplatin, cisplatin, gemcitabine, anthracycline, taxanes, paclitaxel, protein-bound paclitaxel, doxorubicin, docetaxel, vinorelbine, tamoxifen, raloxifene, toremifene, fulvestrant, irinotecan, ixabepilone, temozolmide, topotecan, vincristine, vinblastine, eribulin, mutamycin, capecitabine, capecitabine, anastrozole, exemestane, letrozole, leuprolide, abarelix, buserlin, goserelin, megestrol acetate, risedronate, pamidronate, ibandronate, alendronate, denosumab, zoledronate, trastuzumab, tykerb or bevacizumab, or combinations thereof.

* * * * *

```
SEQUENCE LISTING

Sequence total quantity: 44
SEQ ID NO: 1             moltype = DNA  length = 15
FEATURE                  Location/Qualifiers
misc_feature             1..15
                         note = Synthetic Polynucleotide
source                   1..15
                         mol_type = other DNA
                         organism = synthetic construct
SEQUENCE: 1
ggctgcgggc cattc                                                         15

SEQ ID NO: 2             moltype = DNA  length = 23
FEATURE                  Location/Qualifiers
misc_feature             1..23
                         note = Synthetic Polynucleotide
source                   1..23
                         mol_type = other DNA
                         organism = synthetic construct
SEQUENCE: 2
cttagagact gaggcccatc ctt                                                23

SEQ ID NO: 3             moltype = DNA  length = 16
FEATURE                  Location/Qualifiers
misc_feature             1..16
                         note = Synthetic Polynucleotide
source                   1..16
                         mol_type = other DNA
                         organism = synthetic construct
SEQUENCE: 3
ccagaatcag ggaaac                                                        16

SEQ ID NO: 4             moltype = DNA  length = 23
FEATURE                  Location/Qualifiers
misc_feature             1..23
                         note = Synthetic Polynucleotide
source                   1..23
                         mol_type = other DNA
                         organism = synthetic construct
SEQUENCE: 4
tgttacagga catcaagcgt caa                                                23

SEQ ID NO: 5             moltype = DNA  length = 22
FEATURE                  Location/Qualifiers
misc_feature             1..22
                         note = Synthetic Polynucleotide
```

```
source                  1..22
                        mol_type = other DNA
                        organism = synthetic construct
SEQUENCE: 5
ccaatactcc agaggcaagg aa                                            22

SEQ ID NO: 6            moltype = DNA   length = 16
FEATURE                 Location/Qualifiers
misc_feature            1..16
                        note = Synthetic Polynucleotide
source                  1..16
                        mol_type = other DNA
                        organism = synthetic construct
SEQUENCE: 6
ccaaggtggt tgagcg                                                   16

SEQ ID NO: 7            moltype = DNA   length = 22
FEATURE                 Location/Qualifiers
misc_feature            1..22
                        note = Synthetic Polynucleotide
source                  1..22
                        mol_type = other DNA
                        organism = synthetic construct
SEQUENCE: 7
caaacgcttg tgcgagtaaa tg                                            22

SEQ ID NO: 8            moltype = DNA   length = 18
FEATURE                 Location/Qualifiers
misc_feature            1..18
                        note = Synthetic Polynucleotide
source                  1..18
                        mol_type = other DNA
                        organism = synthetic construct
SEQUENCE: 8
tttgctgcgg ccagtaca                                                 18

SEQ ID NO: 9            moltype = DNA   length = 19
FEATURE                 Location/Qualifiers
misc_feature            1..19
                        note = Synthetic Polynucleotide
source                  1..19
                        mol_type = other DNA
                        organism = synthetic construct
SEQUENCE: 9
agagtcatta acaaggagc                                                19

SEQ ID NO: 10           moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 10
gctggtggtg gtgtcattcc                                               20

SEQ ID NO: 11           moltype = DNA   length = 22
FEATURE                 Location/Qualifiers
misc_feature            1..22
                        note = Synthetic Polynucleotide
source                  1..22
                        mol_type = other DNA
                        organism = synthetic construct
SEQUENCE: 11
tgttgtcctt tcttcccaat ca                                            22

SEQ ID NO: 12           moltype = DNA   length = 15
FEATURE                 Location/Qualifiers
misc_feature            1..15
                        note = Synthetic Polynucleotide
source                  1..15
                        mol_type = other DNA
                        organism = synthetic construct
SEQUENCE: 12
cacatccaca aatct                                                    15
```

```
SEQ ID NO: 13              moltype = DNA  length = 20
FEATURE                    Location/Qualifiers
misc_feature               1..20
                           note = Synthetic Polynucleotide
source                     1..20
                           mol_type = other DNA
                           organism = synthetic construct
SEQUENCE: 13
gaagcagcca tcctcacaca                                                   20

SEQ ID NO: 14              moltype = DNA  length = 22
FEATURE                    Location/Qualifiers
misc_feature               1..22
                           note = Synthetic Polynucleotide
source                     1..22
                           mol_type = other DNA
                           organism = synthetic construct
SEQUENCE: 14
gcctgtagca cctgcacata ga                                                22

SEQ ID NO: 15              moltype = DNA  length = 16
FEATURE                    Location/Qualifiers
misc_feature               1..16
                           note = Synthetic Polynucleotide
source                     1..16
                           mol_type = other DNA
                           organism = synthetic construct
SEQUENCE: 15
acccacgctc ccagat                                                       16

SEQ ID NO: 16              moltype = DNA  length = 17
FEATURE                    Location/Qualifiers
misc_feature               1..17
                           note = Synthetic Polynucleotide
source                     1..17
                           mol_type = other DNA
                           organism = synthetic construct
SEQUENCE: 16
gcccaccacg agcatca                                                      17

SEQ ID NO: 17              moltype = DNA  length = 21
FEATURE                    Location/Qualifiers
misc_feature               1..21
                           note = Synthetic Polynucleotide
source                     1..21
                           mol_type = other DNA
                           organism = synthetic construct
SEQUENCE: 17
cctggactcc taagggcaga t                                                 21

SEQ ID NO: 18              moltype = DNA  length = 14
FEATURE                    Location/Qualifiers
misc_feature               1..14
                           note = Synthetic Polynucleotide
source                     1..14
                           mol_type = other DNA
                           organism = synthetic construct
SEQUENCE: 18
ccagtcctca gccc                                                         14

SEQ ID NO: 19              moltype = DNA  length = 22
FEATURE                    Location/Qualifiers
misc_feature               1..22
                           note = Synthetic Polynucleotide
source                     1..22
                           mol_type = other DNA
                           organism = synthetic construct
SEQUENCE: 19
tccacctccc taccaaaaat tg                                                22

SEQ ID NO: 20              moltype = DNA  length = 20
FEATURE                    Location/Qualifiers
misc_feature               1..20
                           note = Synthetic Polynucleotide
source                     1..20
                           mol_type = other DNA
                           organism = synthetic construct
```

```
SEQUENCE: 20
cccgaattgg gacctaaagc                                                    20

SEQ ID NO: 21           moltype = DNA  length = 17
FEATURE                 Location/Qualifiers
misc_feature            1..17
                        note = Synthetic Polynucleotide
source                  1..17
                        mol_type = other DNA
                        organism = synthetic construct
SEQUENCE: 21
caagtgccta tgcaaac                                                       17

SEQ ID NO: 22           moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 22
caaaggtcag gccgtacaca                                                    20

SEQ ID NO: 23           moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 23
acatctcgaa cctgcccaat                                                    20

SEQ ID NO: 24           moltype = DNA  length = 18
FEATURE                 Location/Qualifiers
misc_feature            1..18
                        note = Synthetic Polynucleotide
source                  1..18
                        mol_type = other DNA
                        organism = synthetic construct
SEQUENCE: 24
ctctgttagg aggcaaat                                                      18

SEQ ID NO: 25           moltype = DNA  length = 22
FEATURE                 Location/Qualifiers
misc_feature            1..22
                        note = Synthetic Polynucleotide
source                  1..22
                        mol_type = other DNA
                        organism = synthetic construct
SEQUENCE: 25
tgcctctgat cgtaggaatt ga                                                 22

SEQ ID NO: 26           moltype = DNA  length = 21
FEATURE                 Location/Qualifiers
misc_feature            1..21
                        note = Synthetic Polynucleotide
source                  1..21
                        mol_type = other DNA
                        organism = synthetic construct
SEQUENCE: 26
cctgccactg tccagttctc a                                                  21

SEQ ID NO: 27           moltype = DNA  length = 15
FEATURE                 Location/Qualifiers
misc_feature            1..15
                        note = Synthetic Polynucleotide
source                  1..15
                        mol_type = other DNA
                        organism = synthetic construct
SEQUENCE: 27
tgtcccgcct tgtgg                                                         15

SEQ ID NO: 28           moltype = DNA  length = 26
FEATURE                 Location/Qualifiers
misc_feature            1..26
                        note = Synthetic Polynucleotide
```

```
source                  1..26
                        mol_type = other DNA
                        organism = synthetic construct
SEQUENCE: 28
gagaaaattg gagaaggtac ctatgg                                              26

SEQ ID NO: 29           moltype = DNA  length = 23
FEATURE                 Location/Qualifiers
misc_feature            1..23
                        note = Synthetic Polynucleotide
source                  1..23
                        mol_type = other DNA
                        organism = synthetic construct
SEQUENCE: 29
tcatggctac cacttgacct gta                                                 23

SEQ ID NO: 30           moltype = DNA  length = 21
FEATURE                 Location/Qualifiers
misc_feature            1..21
                        note = Synthetic Polynucleotide
source                  1..21
                        mol_type = other DNA
                        organism = synthetic construct
SEQUENCE: 30
tgtataaggg tagacacaaa a                                                   21

SEQ ID NO: 31           moltype = DNA  length = 25
FEATURE                 Location/Qualifiers
misc_feature            1..25
                        note = Synthetic Polynucleotide
source                  1..25
                        mol_type = other DNA
                        organism = synthetic construct
SEQUENCE: 31
ataagcgggc gggcggtgaa gagtc                                               25

SEQ ID NO: 32           moltype = DNA  length = 25
FEATURE                 Location/Qualifiers
misc_feature            1..25
                        note = Synthetic Polynucleotide
source                  1..25
                        mol_type = other DNA
                        organism = synthetic construct
SEQUENCE: 32
aacttagtgt tcacaataat gtttc                                               25

SEQ ID NO: 33           moltype = DNA  length = 25
FEATURE                 Location/Qualifiers
misc_feature            1..25
                        note = Synthetic Polynucleotide
source                  1..25
                        mol_type = other DNA
                        organism = synthetic construct
SEQUENCE: 33
gccggcattg ggaatctcgt gacat                                               25

SEQ ID NO: 34           moltype = DNA  length = 25
FEATURE                 Location/Qualifiers
misc_feature            1..25
                        note = Synthetic Polynucleotide
source                  1..25
                        mol_type = other DNA
                        organism = synthetic construct
SEQUENCE: 34
cgggggcaca ggtgcctttg agata                                               25

SEQ ID NO: 35           moltype = DNA  length = 25
FEATURE                 Location/Qualifiers
misc_feature            1..25
                        note = Synthetic Polynucleotide
source                  1..25
                        mol_type = other DNA
                        organism = synthetic construct
SEQUENCE: 35
aagtccggtt tttcaaaggg aataa                                               25
```

```
SEQ ID NO: 36              moltype = DNA   length = 25
FEATURE                    Location/Qualifiers
misc_feature               1..25
                           note = Synthetic Polynucleotide
source                     1..25
                           mol_type = other DNA
                           organism = synthetic construct
SEQUENCE: 36
aagcaaggac tcaacacgga ggtag                                                25

SEQ ID NO: 37              moltype = DNA   length = 25
FEATURE                    Location/Qualifiers
misc_feature               1..25
                           note = Synthetic Polynucleotide
source                     1..25
                           mol_type = other DNA
                           organism = synthetic construct
SEQUENCE: 37
agtggaagag ggactacaaa gtcga                                                25

SEQ ID NO: 38              moltype = DNA   length = 25
FEATURE                    Location/Qualifiers
misc_feature               1..25
                           note = Synthetic Polynucleotide
source                     1..25
                           mol_type = other DNA
                           organism = synthetic construct
SEQUENCE: 38
gcgcacgggc aagtacgtgt acttc                                                25

SEQ ID NO: 39              moltype = DNA   length = 25
FEATURE                    Location/Qualifiers
misc_feature               1..25
                           note = Synthetic Polynucleotide
source                     1..25
                           mol_type = other DNA
                           organism = synthetic construct
SEQUENCE: 39
taagaaatga aaagaacaa gagct                                                 25

SEQ ID NO: 40              moltype = DNA   length = 25
FEATURE                    Location/Qualifiers
misc_feature               1..25
                           note = Synthetic Polynucleotide
source                     1..25
                           mol_type = other DNA
                           organism = synthetic construct
SEQUENCE: 40
cgtccctctg gatggccgcc ccatg                                                25

SEQ ID NO: 41              moltype = DNA   length = 25
FEATURE                    Location/Qualifiers
misc_feature               1..25
                           note = Synthetic Polynucleotide
source                     1..25
                           mol_type = other DNA
                           organism = synthetic construct
SEQUENCE: 41
caagaggaag agagagaccc tcact                                                25

SEQ ID NO: 42              moltype = DNA   length = 25
FEATURE                    Location/Qualifiers
misc_feature               1..25
                           note = Synthetic Polynucleotide
source                     1..25
                           mol_type = other DNA
                           organism = synthetic construct
SEQUENCE: 42
ggactaatta tggacaggac tgaac                                                25

SEQ ID NO: 43              moltype = DNA   length = 25
FEATURE                    Location/Qualifiers
misc_feature               1..25
                           note = Synthetic Polynucleotide
source                     1..25
                           mol_type = other DNA
                           organism = synthetic construct
```

```
SEQUENCE: 43
tgaacagtca ccgacgagag tgctg                                                25

SEQ ID NO: 44          moltype = DNA  length = 25
FEATURE                Location/Qualifiers
misc_feature           1..25
                       note = Synthetic Polynucleotide
source                 1..25
                       mol_type = other DNA
                       organism = synthetic construct
SEQUENCE: 44
aatcccaagc ggtttgctgc ggtaa                                                25
```